United States Patent
Lee et al.

(10) Patent No.: US 10,694,964 B2
(45) Date of Patent: Jun. 30, 2020

(54) NEURAL SPIKE SCANNING FOR HIGH-DENSITY IMPLANTABLE NEURAL RECORDING SYSTEMS

(71) Applicant: International Business Machines Corporation, Armonk, NY (US)

(72) Inventors: Hyung-Min Lee, Seoul (KR); Mounir Meghelli, Tarrytown, NY (US); Jonathan E. Proesel, Mt. Vernon, NY (US)

(73) Assignee: International Business Machines Corporation, Armonk, NY (US)

(*) Notice: Subject to any disclaimer, the term of this patent is extended or adjusted under 35 U.S.C. 154(b) by 338 days.

(21) Appl. No.: 15/695,408

(22) Filed: Sep. 5, 2017

(65) Prior Publication Data
US 2019/0069787 A1    Mar. 7, 2019

(51) Int. Cl.
*A61B 5/04*    (2006.01)
*A61B 5/00*    (2006.01)
*A61B 5/07*    (2006.01)

(52) U.S. Cl.
CPC ........ *A61B 5/04001* (2013.01); *A61B 5/0031* (2013.01); *A61B 5/04004* (2013.01); *A61B 5/04017* (2013.01); *A61B 5/076* (2013.01); *A61B 5/6868* (2013.01); *A61B 2562/0219* (2013.01); *A61B 2562/046* (2013.01)

(58) Field of Classification Search
CPC .............. A61B 5/0031; A61B 5/04001; A61B 5/04004; A61B 5/04017; A61B 5/6868
See application file for complete search history.

(56) References Cited

U.S. PATENT DOCUMENTS

| | | |
|---|---|---|
| 2005/0090756 A1 | 4/2005 | Wolf et al. |
| 2009/0004685 A1 | 1/2009 | Huys et al. |
| 2009/0265287 A1 | 10/2009 | Haas |
| 2010/0081958 A1 | 4/2010 | She |
| 2015/0231397 A1 | 8/2015 | Nudo et al. |
| 2015/0369634 A1 | 12/2015 | Amrutur et al. |
| 2016/0073887 A1 | 3/2016 | Lee et al. |

FOREIGN PATENT DOCUMENTS

| | | |
|---|---|---|
| CN | 103190903 A | 7/2013 |
| CN | 103961094 A | 8/2014 |
| WO | 2005092183 A1 | 10/2005 |
| WO | 2015114347 A1 | 8/2015 |
| WO | 2016187039 A1 | 11/2016 |

OTHER PUBLICATIONS

Sodagar, Amir M. et al., "An implantable 64-channel wireless microsystem for single-unit neural recording", IEEE Journal of Solid-State Circuits 44.9 (2009): 2591-2604.

*Primary Examiner* — Christine H Matthews
(74) *Attorney, Agent, or Firm* — Harrington & Smith

(57) ABSTRACT

A neural signal recording device includes a scan-mode circuit and a read-mode circuit. The scan-mode circuit detects neural spike activity within any M groups of electrodes selected from a total of N electrodes that are coupled to a brain. The read-mode circuit then records all neural spike signals present within any one of the M groups of electrodes where the neural spike activity is detected by the scan-mode circuit, whereby less than N electrodes are recorded at any one time by the neural signal recording device.

13 Claims, 11 Drawing Sheets

NEURAL SPIKE SCANNING FOR HIGH-DENSITY IMPLANTABLE NEURAL RECORDING SYSTEMS

BACKGROUND

The present invention generally relates to neurological brain activity, and more particularly, to recording neural signals received from multiple electrodes coupled to the brain.

Electrical neural signals (e.g., neural spike signals) can be directly recorded from the brain using, for example, an implantable system (i.e., an implanted chip). However, the provision of adequate spatial and temporal resolution for brain-mapping can require the real-time monitoring of a large number of electrodes in contact with the brain.

SUMMARY

According to one or more embodiments, recording neural signals (e.g., neural spikes) from a large number of electrodes using a smaller number of recording channels are provided, whereby neural signal activity (e.g., neural spike signals) on selected groups of electrodes are scanned and then subsequently recorded.

According to one or more embodiments, a neural signal recording device includes a scan-mode circuit that detects neural spike activity at one or more M groups of electrodes selected from a total of N electrodes that are coupled to a brain. The neural signal recording device also includes a read-mode circuit that records all neural spike signals present at the one or more M groups of electrodes where the neural spike activity is detected by the scan-mode circuit, whereby less than N electrodes are recorded at any one time by the read-mode circuit.

According to one embodiment, a method of recording neural spike signals from a brain includes dividing N electrodes coupled to the brain into M groups, the M groups each having a plurality of electrodes; combining signals received from the plurality of electrodes corresponding to each one of the M groups of electrodes to generate M signal outputs; scanning all of the M signal outputs for the detection of neural spike signals; and responsive to the detection of the neural spike signals within any one or more of the M signal outputs, recording neural spike activity on all of the plurality of electrodes corresponding to the any one or more of the M groups of electrodes where the neural spike signals are detected, whereby less than N electrodes are recorded at any one time.

According to one or more other embodiments, a neural signal recording device includes a first signal combiner circuit having a first group of inputs and a first output, where the first group of inputs are coupled to a first group of $C_1$ electrodes of N electrodes coupled to a brain, and the first output combines one or more first neural spike signals received from the first group of $C_1$ electrodes; a second signal combiner circuit having a second group of inputs and a second output, where the second group of inputs are coupled to a second group of $C_2$ electrodes of the N electrodes, and the second output combines one or more second neural spike signals received from the second group of $C_2$ electrodes; a plurality of neural signal detection circuits respectively coupled to the first and the second outputs for detecting one or more neural spike signals from either the $C_1$ electrodes or the $C_2$ electrodes; and a switch matrix coupled to the N electrodes that either routes only all of the first group of $C_1$ electrodes for signal recording responsive to the detecting of the one or more first neural spike signals from the $C_1$ electrodes or only routes all of the second group of $C_2$ electrodes for signal recording responsive to the detecting of the one or more second neural spike signals from the $C_2$ electrodes, where $C_1<N$ and $C_2<N$.

According to one or more other embodiments, a computer-implemented method of recording neural spike signals from a brain is provided, whereby the method includes generating a scan control signal for enabling the receiving of a plurality of M output signals, where each of the plurality of M output signals are based on a combining of a plurality of input signals respectively received from a plurality of N electrodes coupled to the brain; receiving digitized versions of the received plurality of M output signals for detecting neural spike signals from one or more of the plurality of M output signals; and generating a read control signal for enabling a signal recording from all of the plurality of electrodes corresponding to the one or more of the plurality M output signals having the detected neural spike signals. During the signal recording, the receiving of the plurality of output signals is disabled by the scan control signal such that $M<N$.

According to one or more other embodiments, a computer program product for recording neural spike signals from a brain is provided, whereby the computer program product includes one or more non-transitory computer-readable storage devices and program instructions stored on at least one of the one or more non-transitory storage devices, such that the program instructions are executable by a processor. The program instructions include instructions to generate a scan control signal for enabling the receiving of a plurality of M output signals, where each of the plurality of M output signals are based on a combining of a plurality of input signals respectively received from a plurality of N electrodes coupled to the brain; instructions to receive digitized versions of the received plurality of M output signals for detecting neural spike signals from one or more of the plurality of M output signals; and instructions to generate a read control signal for enabling a signal recording from all of the plurality of electrodes corresponding to the one or more of the plurality M output signals having the detected neural spike signals, whereby during the signal recording, the receiving of the plurality of output signals is disabled by the scan control signal, and wherein $M<N$.

BRIEF DESCRIPTION OF THE SEVERAL VIEWS OF THE DRAWINGS

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1:
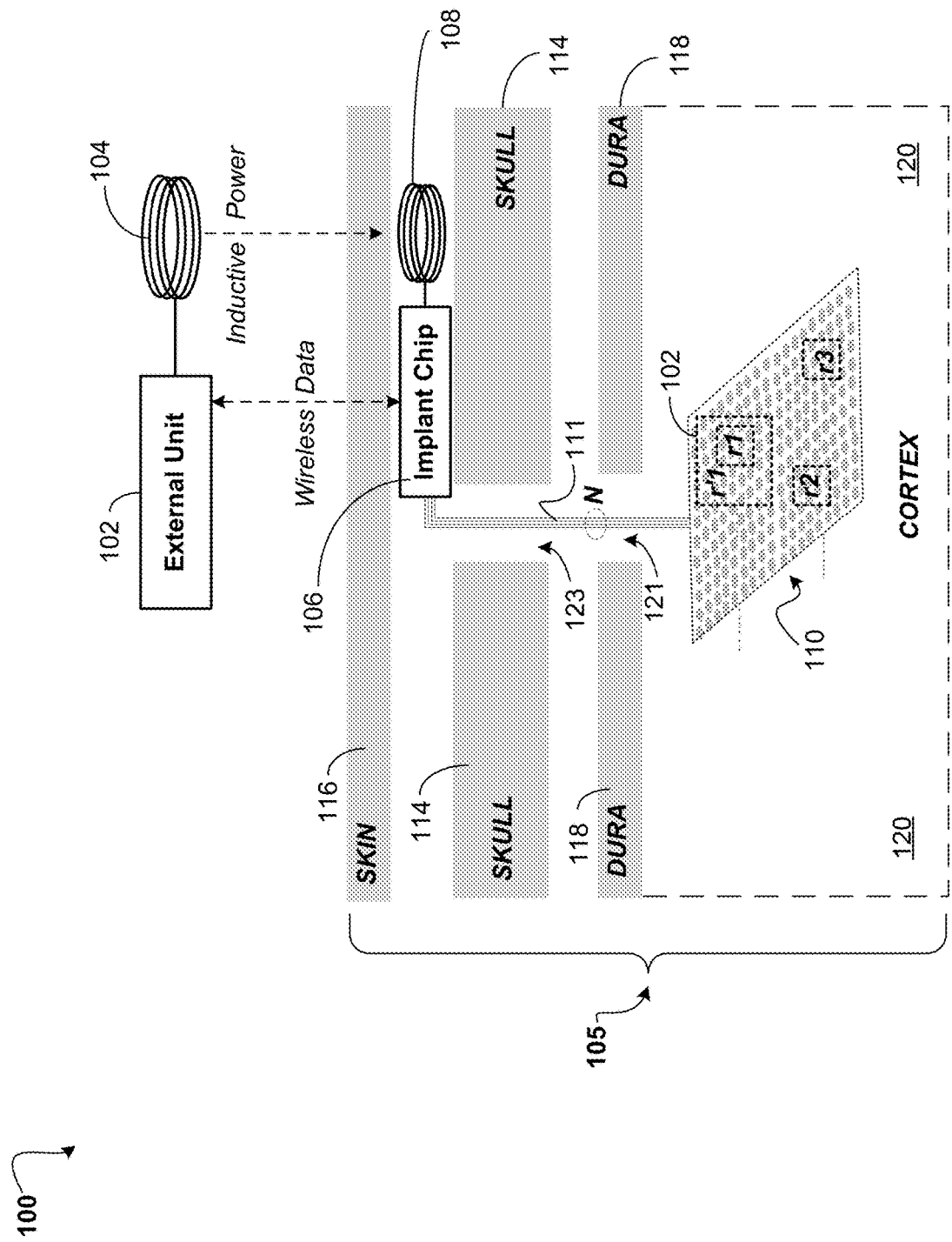
FIG. 1 shows a block diagram of a system for monitoring neurological brain activity, according to one exemplary embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a circuit, a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The one or more exemplary embodiments described herein are directed to, among other things, recording neural signals (e.g., neural spikes) from a large number of electrodes using a smaller number of recording channels. According to one example, 512-electrodes can be processed using a reduced (i.e., factor of 8) number of 64-channels. In general, N-electrodes can be recorded using a reduced number of M-channels.

FIG. 1 shows a block diagram of a system 100 for monitoring neurological brain activity, according to one exemplary embodiment. As illustrated, the system for monitoring neurological brain activity 100 may include an external unit 102 having inductive power coupling device 104, an implant chip 106 having inductive power coupling device 108, and a plurality of N electrodes 110 each having signal conducting means 111 for coupling to the implant chip 106.

As depicted, based on a given subject's head 105, the implant chip 106 may be placed between the surface of the subject's skull 114 and the skin 116 covering the skull 114. The plurality of N electrodes 110 are coupled to the cortex region 120 of the subject's brain, while the signal conducting means 111 of the plurality of N electrodes are passed through both an opening 121 in the dura 118 covering the outer surface of the cortex 120 and an opening 123 created in the skull 114.

In operation, the plurality of N electrodes 110 and their corresponding signal conducting means 111 receive and transmit neurological signal activity (e.g., neural spike signals) from the cortex region 120 to the implant chip 106. The implant chip 106 may then subsequently process and record any neurological signals (e.g., neural spikes) received from, for example, different areas r1, r2, r3 of the cortex region 120. Data associated with the processed and recorded neurological signals (e.g., neural spikes) can then be wirelessly transmitted by the implant chip 106 to the external unit 102, which may be any type of computer device (e.g., laptop, desktop, tablet, mobile device, etc.). In order to facilitate the wireless transmission of such data, the external unit 102, or computer device, causes a current to energize inductive power coupling device 104. An electromagnetic field generated by the energized inductive power coupling device 104 then induces current within the inductive power coupling device 108 coupled to the implant chip 106. The implant chip 106 can subsequently utilize this induced current to power a wireless transceiver located within the implant device 106 for data transmission/reception purposes.

The external unit 102 may include software programming for further processing the data associated with the processed and recorded neurological signals (e.g., neural spikes). For example, the external unit 102 may pole the implant chip at regular intervals in order to receive and further process any neurological signals received from the cortex region 120. According to another example, the external unit 102 may provide software updates and operational configurations to the implant device 106.

Figure 2:
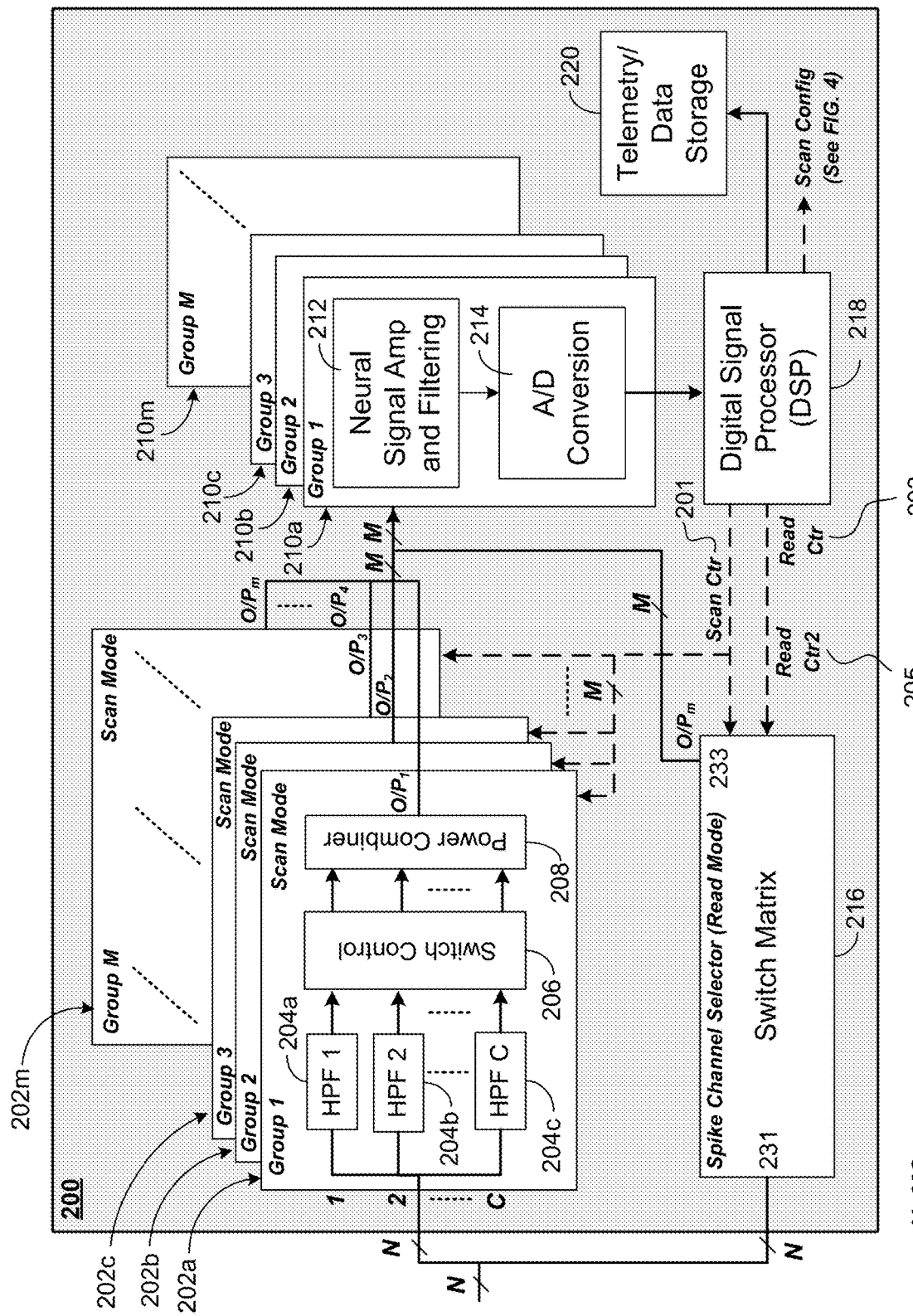
FIG. 2 shows a neural recording device associated with FIG. 1's system for monitoring neurological brain activity, according to one exemplary embodiment.

FIG. 2 shows a neural recording device 200 associated with FIG. 1's exemplary system 100 for monitoring neurological brain activity, according to one embodiment. The neural recording device 200 includes both scan mode and read mode circuits for detecting and recording neural spike signals associated with a subject's brain (e.g., FIG. 1: cortex region 120). The scan mode and read mode circuits may contemplate using separate devices or circuits to provide the scan mode and read mode operations. Alternatively, however, the scan mode and read mode circuits may contemplate using common/shared devices or circuits during the scan mode and read mode operations.

The scan mode circuit detects neural spike activity within any of the M groups of electrodes selected from a total of N electrodes that are coupled to the brain. Accordingly, the total of N electrodes that are coupled to the brain are divided into M groups, whereby each of the M groups have C electrodes for detection, such that in some embodiments, N=C×M.

The scan mode circuit includes a plurality of M signal combining circuits 202a-202m that each detect the occurrence of one or more neural spike signals occurring within a corresponding group of electrodes taken from the total of N electrodes coupled to the brain. For example, signal combining circuit 202a detects the occurrence of one or more neural spike signals occurring within a first group (i.e., Group 1) of 1 to C electrodes, signal combining circuit 202b detects the occurrence of one or more neural spike signals occurring within a second group (i.e., Group 2) of other 1 to C electrodes, signal combining circuit 202c detects the occurrence of one or more neural spike signals occurring within a third group (i.e., Group 3) of other 1 to C electrodes, etc.

Each of the plurality of M signal combining circuits 202a-202m aggregate the signals received from respective input electrodes 1 to C. For example, signal combining circuit 202a includes high-pass filters 204a-204c, a switch control unit 206, and a power combiner 208. Accordingly, signals received from input electrodes 1 to C are each filtered in order to pass the higher frequency neural spike signals, while filtering other spurious unwanted signals. Thus, within signal combining circuit 202a, high-pass filter 204a filters neural spike signals that may be received from electrode 1, high-pass filter 204b filters neural spike signals that may be received from electrode 2, etc., until high-pass filter 204c filters neural spike signals that may be received from electrode C. The filtered outputs from the high-pass filters 204a-204c are coupled to the switch control unit 206, which enables or inhibits the transmission of the filtered outputs to the power combiner 208. The power combiner 208 may then couple any of the neural spikes signals received from high-pass filters 204a-204c to a single output $O/P_1$. The power combiner 208 output $O/P_1$ thus enables the aggregation of any neural spike activity within the group of 1 to C electrodes regardless of whether only a single neural spike signal is received (e.g., neural spike received from only electrode 1), a few neural spike signals are received (e.g., neural spikes received from electrodes 1, 3, and 6), or all the neural spike signals are received (e.g., neural spikes received from every electrode 1 to C). Signal combining circuits 202b-202m may also include the same or similar high-pass filters, switch control units, and power combiners to that of signal combining circuit 202a described above.

The scan mode circuit may also include a plurality of M neural signal detection circuits 210a-210m that are each coupled to a respective one of the signal combining circuits 202a-202m. For example, neural signal detection circuit 210a is coupled to signal combining circuit 202a, neural signal detection circuit 210b is coupled to signal combining circuit 202b, neural signal detection circuit 210c is coupled to signal combining circuit 202c, etc. Thus, for M signal combining circuits 210a-210m, M neural signal detection circuits 202a-202m are utilized, whereby each of the M neural signal detection circuits 210a-210m detect the occurrence of any neural spike signals output from a respective one of the M signal combining circuits 202a-202m to which it is coupled. For example, neural signal detection circuit 210a detects the occurrence of any neural spike signals output from signal combining circuit 202a, neural signal detection circuit 210b detects the occurrence of any neural spike signals output from signal combining circuit 202b, neural signal detection circuit 210c detects the occurrence of any neural spike signals output from signal combining circuit 202c, etc.

Each of the plurality of M neural signal detection circuits 210a-210m may include a filtering and signal amplification circuit 212 (i.e., a preprocessing stage) and an analog-to-digital (A/D) convertor circuit 214 coupled to the filtering and signal amplification circuit 212. The filtering and signal amplification circuit 212 may include a bandpass filter that is configured to pass a range of frequency components corresponding to the presence of neural spike signals, while suppressing other unwanted spurious signals (e.g., noise reduction). Any neural spike signals passed by the bandpass filter are then amplified by an amplifier circuit prior to being coupled to and received by the analog-to-digital (A/D) convertor circuit 214. At the analog-to-digital (A/D) convertor circuit 214, any filtered and amplified neural spike signals are converted to digitized neural spike signals. Thus, detected neural spike signals are converted into a digital format for facilitating a read mode operation of the neural recording device 200. Accordingly, during the read mode, one or more neural spike signals present on all of the 1 to C electrodes associated with each of the M groups exhibiting a detected spike signal are recorded for further neurologically-related analysis, as described in more detail in the following paragraphs. As such, each of the M groups that do not have any detected neural spike signals are not considered for signal recording.

In some embodiments, the analog-to-digital (A/D) convertor circuit 214 may contemplate the use of a digital threshold comparison capability, whereby the digitized signals are compared with a digital threshold value in order to ensure that neural spikes, and not an unwanted signal components, have been detected and digitized. In other embodiments, such a digital threshold comparison capability can be incorporated within other circuitry/devices (e.g., DSP 218) associated with the neural recording device 200.

The read mode circuit records all neural spike signals present within any one of the M groups of electrodes where neural spike activity is detected by the scan mode circuit. In particular, when a neural spike signal is detected on at least one of the electrodes within one of the M groups of electrodes, all of the electrodes within that group are routed through for signal recordation. Accordingly, routing and signal recordation is only applied to groups within the M groups where neural signals are detected, while signal routing and recordation is suspended for any of the groups within the M groups with no detected neural signal activity. Thus, routing and recordation of neural signals from the N electrodes can be achieved using a reduced number of M channels.

The read mode circuit may include a switch matrix 216 and a digital signal processor (DSP) 218. The read mode circuit may additionally include a telemetry and data storage unit 220. As depicted, the N electrodes coupled to the brain are also received as inputs to the switch matrix 216. However, from the N inputs, the switch matrix 216 has a reduced number of M outputs $O/P_m$ that are also coupled to the plurality of M neural signal detection circuits 210a-210m associated with the scan mode circuit. As such, the illustrated exemplary embodiment includes a circuit/device/component (i.e., neural signal detection circuits 210a-210m) that can form part of both the read mode circuit and the scan mode circuit. It should however be appreciated, that according to other embodiments, the M outputs of the switch matrix 216 may be coupled to M other neural signal detection circuits (not shown) that operate in a similar or identical manner to that of neural signal detection circuits 210a-210m. As previously described, any neural spike signals routed to the M outputs of the switch matrix 216 are filtered, amplified, and digitized (i.e., front end processing) by a respective one of the plurality of M neural signal detection circuits 210a-210m.

The DSP 218 may include any circuit capable of processing digital signals (e.g., neural signals, etc.) and generating commands for the execution of the neural recording device 200 operability. In particular, the DSP 218 may initiate, via a read control signal 203, the routing operation of the switch matrix 216 based on the scan circuit detecting which groups of the M groups are exhibiting neural switch activity. Moreover, the DSP 218 may active and deactivate the operation of the M signal combining circuits 202a-202m and consequently the scan control circuit, via a scan control signal 201. Once the routing operation of the switch matrix 216 is initiated, neural signals routed to switch outputs $O/P_m$ are detected and sent to the DSP 218 from the neural signal detection circuits 210a-210m. For example, if neural spike activity is detected on only signal combining circuit 202a (Group 1) and signal combining circuit 202b (Group 2), the signals associated with the 1 to C electrodes coupled to combining circuits 202a and 202b are routed to the switch matrix 216 outputs $O/P_m$. Using a numerical example, assume 8 electrodes (i.e., C=8) are coupled to circuit 202a and 8 electrodes (i.e., C=8) are to coupled 202b. Therefore, a total of 16 electrodes corresponding to the inputs of both combining circuits 202a, 202b are routed to 16 outputs of the switch's M outputs $O/P_m$. These 16 outputs are then processed by 16 neural signal detection circuits, whereby the processed outputs from these 16 neural signal detection circuits are received and recorded by the DSP 218.

The recording process may include storing the neural spike digital values of the routed 1 to C electrodes corresponding to the one or more signal combining circuits that exhibited neural spike activity during the scan mode. Using the above example, during the recording process, the DSP 216 stores the digital values associated with any of the neural spike signals detected on the 16 input electrodes of combining circuits 202a and 202b. The DSP 218 may store the neural spike digital values either within memory located on the DSP 218, or alternatively, the DSP 218 may forward this data to the data storage and telemetry unit 220. The recording process may also include storing additional information associated with each of the neural spike digital values. For example, data corresponding to each neural signal's time/date of recording (e.g., Mar. 31, 2016 at 10:30 AM) and electrode number (e.g., electrode 1006) may be stored with each of the neural spike digital values.

According to some embodiments, the stored data corresponding to each neural signal's time/date of recording (e.g., Mar. 31, 2016 at 10:30 AM), electrode number (e.g., electrode 1006), and digital value may be transmitted via the telemetry functionality of unit 220. In other embodiments, the DSP 218 may include an embedded transceiver circuit, whereby the stored data corresponding to each neural signal's time/date of recording (e.g., Mar. 31, 2016 at 10:30 AM), electrode number (e.g., electrode 1006), and digital value may be transmitted using such a transceiver. According to yet another embodiment, both the telemetry/data storage unit 220 and the DSP's 218 transceiver can provide simultaneous transmission means for, among other things, each neural signal's time/date of recording (e.g., Mar. 31, 2016 at 10:30 AM), electrode number (e.g., electrode #1006), and digital value. In such an embodiment, the throughput of neural spike data transmitted from the neural recording device 200 to the external unit 102 (FIG. 1) can be dynamically increased to facilitate real-time monitoring of neurological activity.

Although the scan mode and read mode circuits have been described using the exemplary embodiment of neural recording device 200, it will be appreciated that such scan and read mode functionality can be implemented using alternative hardware, software, firmware, or any combination thereof.

FIGS. 3A-3D are flow diagrams associated with the operation of a neural recording system, according to one exemplary embodiment. The following operational description of a neural recording system is facilitated with the aid of the exemplary neural recording system of FIG. 2, although any other hardware, software, or hardware/software-based neural recording system may be contemplated.

Figure 3A:
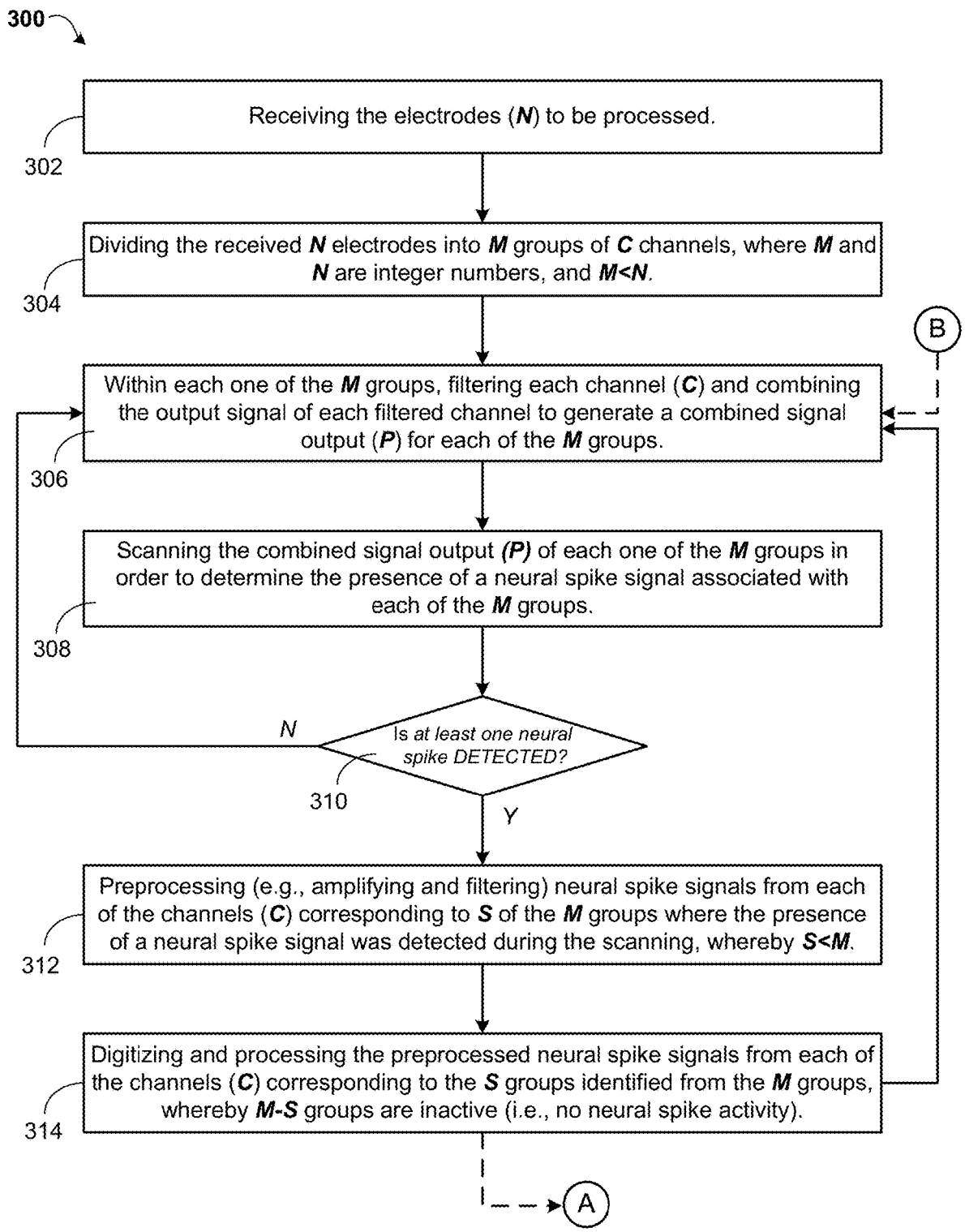
FIGS. 3A-3D are functional flow diagrams associated with the operation of a neural recording device, according to one exemplary embodiment.

Referring to FIG. 3A, at 302, a finite number of N electrodes to be processed are received. For example, the N electrodes (FIG. 2) are received by the signal combining circuits 202a-202m (FIG. 2) and the switch matrix 216 (FIG. 2).

At 304, the received N electrodes are divided into M groups of electrodes each having C electrodes as input channels (e.g., N=M×C), where M and N are integer numbers, and M<N. Using a numerical example, N=512 electrodes may be divided into M=64 groups each having C=8 electrodes as input channels. As such, the N=512 electrodes are received by M=64 signal combining circuits 202a-202m (FIG. 2), whereby each of the M=64 signal combining circuits 202a-202m (FIG. 2) include C=8 input electrodes associated with the N=512 electrodes. As further depicted in FIG. 2, the N=512 electrodes are also received as inputs to the switch matrix 216.

At 306, within each one of the M groups of electrodes, a combined signal output (P) for each of the M groups is generated by filtering each input channel (C) within the group and combining the output signal of each of the filtered channels. For example, within signal combining circuit 202a (FIG. 2), O/P$_1$ (FIG. 2) is generated by filtering each of input channels 1 to C (FIG. 2) and combining such filtered input channels via power combiner 208 (FIG. 2). Combined signal outputs O/P$_2$-O/P$_m$ (FIG. 2) for the remaining combining circuits are thus generated in the same or similar manner. Thus, M outputs O/P$_1$-O/P$_m$ (FIG. 2) are generated from the signal combining circuits 202a-202m (FIG. 2).

At 308, the combined signal output (P) of each one of the M groups are scanned in order to determine the presence of one or more neural spike signals associated with each of the M groups. For example, using neural signal detection circuits 210a-210m (FIG. 2), the combined signal outputs O/P$_1$-O/P$_m$ (FIG. 2) received from each of the respective combining circuits 202a-202m (FIG. 2) are scanned in order to determine the presence of one or more neural spike signals. For example, neural signal detection circuit 210a (FIG. 2) determines whether one or more neural spike signals can be detected from the output O/P$_1$ of combining circuit 202a (FIG. 2), neural signal detection circuit 210b (FIG. 2) determines whether one or more neural spike signals can be detected from the output O/P$_2$ of combining circuit 202b (FIG. 2), neural signal detection circuit 210c (FIG. 2) determines whether one or more neural spike signals can be detected from the output O/P$_3$ of combining circuit 202c (FIG. 2), etc. Neural signal detection circuit 210a (FIG. 2) determines the presence of one or more neural spike signals by bandpass filtering, amplifying, and digitizing signals that are received from the output O/P$_1$; neural signal detection circuit 210b (FIG. 2) determines the presence of one or more neural spike signals by bandpass filtering, amplifying, and digitizing signals that are received from the output O/P$_2$; neural signal detection circuit 210c (FIG. 2) determines the presence of one or more neural spike signals by bandpass filtering, amplifying, and digitizing signals that are received from the output O/P$_3$, etc. At these outputs O/P$_1$-O/P$_m$ (FIG. 2), the digitized signals having a value above a certain threshold (e.g., above the noise level or spurious signals conducted on the electrodes) may thus correspond to detected neural spike signals.

At 310, it is determined whether a neural spike signal is present at any of the combined signal outputs. For example, based on the scanning described above in relation to process 308, it is determined whether a neural spike signal or signals is present on one or more of the combined signal outputs O/P$_1$-O/P$_m$ (FIG. 2). For example, based on the scanning, it may be determined that neural spike signals are present on only O/P$_1$, O/P$_2$, and O/P$_3$ (FIG. 2). If no neural spike signals are present on any of the outputs O/P$_1$-O/P$_m$ (FIG. 2), then processing returns to 306 and 308, where signal combining and scanning is continued until neural spike signal activity on any of the combined outputs O/P$_1$-O/P$_m$ (FIG. 2) is detected.

At 312, based on the detection of neural spike signals during process 310, neural spike signals from each of the channels (C) corresponding to S of the M groups where the presence of one or more neural spike signals was detected during the scanning are preprocessed (e.g., amplified and filtered), whereby S<M. For example, during the scanning, one or more neural spike signals may be detected at only output O/P$_1$ of combining circuit 202a (FIG. 2), O/P$_2$ of combining circuit 202b (FIG. 2), and O/P$_3$ of combining circuit 202c (FIG. 2). Accordingly, the DSP 218 (FIG. 2) may then generate a read control 203 (FIG. 2) signal to the switch matrix 216 (FIG. 2) in order to enable the routing of all the electrodes (1 to C) that are input to these combining circuits 202a, 202b, 202c where one or more neural spike signals were detected during the scanning process from the their respective outputs O/P$_2$, O/P$_2$, O/P$_3$. If C=8, then each of combining circuits 202a, 202b, and 202c, include '8' electrodes that are routed by the switch 216. Therefore, a total of '24' electrodes (3×8) are routed to '24' corresponding neural signal detection circuits 210a-210m (FIG. 2) for preprocessing, whereby electrodes conducting neural spike signals are filtered and amplified. As such, in the above example, S=3 of the M=64 groups are preprocessed. Thus, based on such an exemplary configuration, a reduced number of electrodes are processed at any given time, since routing and recording are initiated only for groups of electrodes exhibiting signal activity.

At 314, the preprocessed neural spike signals from each of the channels (C) corresponding to the S groups identified from the M groups are digitized and may be further processed (e.g., whereby M-S groups are inactive (i.e., no neural spike activity). Using the above example, the total of '24' electrodes (3×8) that are routed to the '24' corresponding neural signal detection circuits 210a-210m (FIG. 2) are digitized and stored following the filtering and amplification (i.e., preprocessing). Thus, M-S (64-3=61) groups are inactive and not required to be routed, preprocessed, and processed. It may be appreciated that in some embodiments, preprocessing may not be required. In such an embodiment, neural spike signals that are routed are directly digitized and stored. The processing can include not only the storing of the digitized neural signals (i.e., digital values), but also providing several other actions, such as but not limited to, adding metadata (e.g., timestamp, date, electrode information, etc.), adding communication protocol information, and controlling the data transmission of the stored digitized neural signals.

Figure 3B:
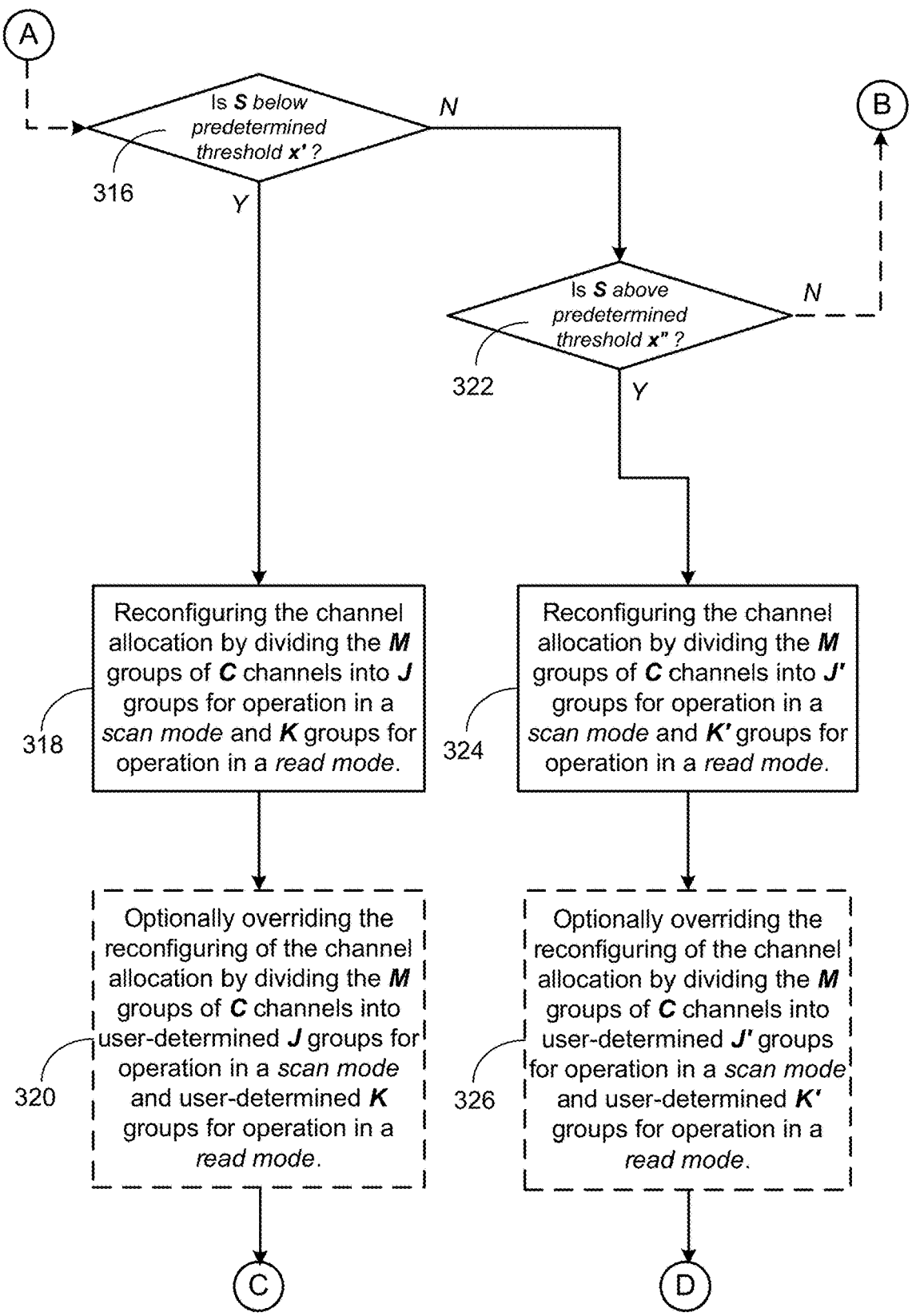

Referring now to FIG. 3B, according one exemplary embodiment, the scanning and recording process may be conditionally reconfigured to include certain groups of electrodes that are in a read only mode (continuous routing and recording), while other groups of electrodes are assigned as operating in the scan and read mode configuration described in relation to FIG. 3A. Additionally, the conditional reconfiguration can be overridden in favor of a manual reconfiguration process where a user may determine which groups of electrodes are in a read only mode (continuous routing and recording), and what groups of electrodes are to be assigned as operating in the scan and subsequent read mode configuration.

At 316 it is determined whether the S number of groups where one or more neural spike signals were each detected, falls below a predetermined threshold x. For example, from among 64 groups (e.g., M=64) each having 8 electrodes (e.g., C=8), predetermined threshold x' may be set to include a value of '3'. Accordingly, if less than '3' groups (e.g., S=2) indicate the presence of neural spike signal activity, the reconfiguration process of 318 occurs.

Thus, at 318, channel allocation is reconfigured by dividing the M groups of C input channels (or electrodes) into J groups for operation in a scan mode and K groups for operation in a read mode (i.e., M=K+J). For example, based on a determination that S=3 (i.e., S<x'=3) groups out of M=64 are exhibiting neural spike signal activity, K=2 groups may be designate to operate in a read mode, whereby their input electrodes (2 groups×8 electrodes=16 total-electrodes) are each continuously routed through the switch 216 to a respective one of the neural signal detection circuits 210a-210m (FIG. 2) and the DSP 218. Here, continuously routed means that the K groups are recorded without the groups being scanned for the detection of a neural spike signal prior to being routed through for recording purposes. As such, the remaining J groups (J=M-K=64-2=62) are operated in a scan mode, whereby these J groups are evaluated using combining circuits (e.g., FIG. 2: 202a-202m) and neural signal detection circuits (e.g., FIG. 2: 210a-210m) for detecting the presence of neural spike signals. In this configuration, if a limited region or regions of the brain, and thus a limited number of groups, are exhibiting neural activity, it may be desirable to maintain a constant recording of these particular groups without the delay of scanning and then reading the signals.

At 320, the conditional channel allocation of process 318 may be optionally overridden by dividing the M groups of C input channels (or electrodes) into J groups for operation in a scan mode and K groups for operation in a read mode (i.e., M=K+J). For example, K=3 groups may be user-designated to operate in a read mode, whereby their input electrodes (3 groups×8 electrodes=24 total-electrodes) are each continuously routed through the switch 216 to a respective one of the neural signal detection circuits 210a-210m (FIG. 2) and the DSP 218. As such, the remaining J groups (J=M-K=64-3=61) are operated in a scan mode, whereby these J groups are evaluated using combining circuits (e.g., FIG. 2: 202a-202m) and neural signal detection circuits (e.g., FIG. 2: 210a-210m) for detecting the presence of neural spike signals. In this override configuration, however, if a limited region or regions of the brain and thus a limited number of groups are exhibiting neural activity, a constant recording of user-selected groups may be adopted without the delay of scanning and then reading the neural spike signals. Since the conditional process of 318 allocates a predetermined allocation of J and K groups, process 320 allows a user to vary the designation of the J and K groups based on further observation of the neural activity.

If, however, at 316 it is determined that the S number of groups where one or more neural spike signals were each detected is above the predetermined threshold x', then the process moves to 322. Accordingly, at 322 it is determined whether the S number of groups where one or more neural spike signals were each detected, exceeds another higher predetermined threshold x". For example, from among 64 groups (e.g., M=64) each having 8 electrodes (e.g., C=8), predetermined threshold x" may be set to include a value of '5'. Accordingly, if more than '5' groups (e.g., S=6) indicate the presence of neural spike signal activity, the reconfiguration process of 324 occurs.

Thus, at 324, channel allocation is reconfigured by dividing the M groups of C input channels (or electrodes) into J' groups for operation in a scan mode and K' groups for operation in a read mode (i.e., M=K'+J'). For example, based on a determination that S=6 (i.e., S>x"=5) groups out of M=64 are exhibiting neural spike signal activity, K'=5 groups may be designated to operate in a read mode, whereby their input electrodes (5 groups×8 electrodes=40 total-electrodes) are each continuously routed through the switch 216 to a respective one of the neural signal detection circuits 210a-210m (FIG. 2) and the DSP 218. Here, continuously routed means that the K' groups are recorded without the groups being scanned for the detection of a neural spike signal prior to being routed through for recording purposes. As such, the remaining J' groups (J'=M-K'=64-5=59) are operated in a scan mode, whereby these J' groups are evaluated using combining circuits (e.g., FIG. 2: 202a-202m) and neural signal detection circuits (e.g., FIG. 2: 210a-210m) for detecting the presence of neural spike signals. In this configuration, if an extended region or regions of the brain, and thus a greater number of groups, are exhibiting neural activity, it may be desirable to maintain a constant recording of these particular groups without the delay of scanning and then reading the signals.

At 326, the conditional channel allocation of process 318 may be optionally overridden by dividing the M groups of C input channels (or electrodes) into J' groups for operation in a scan mode and K groups for operation in a read mode (i.e., M=K'+J'). For example, K'=6 groups may be user-designated to operate in a read mode, whereby their input electrodes (6 groups×8 electrodes=48 total-electrodes) are each continuously routed through the switch 216 to a respective one of the neural signal detection circuits 210a-210m (FIG. 2) and the DSP 218. As such, the remaining J groups (J'=M−K'=64−6=58) are operated in a scan mode, whereby these J' groups are evaluated using combining circuits (e.g., FIG. 2: 202a-202m) and neural signal detection circuits (e.g., FIG. 2: 210a-210m) for detecting the presence of neural spike signals. In this override configuration, however, if an extended region or regions of the brain and thus a greater number of groups are exhibiting neural activity, a constant recording of user-selected groups may be adopted without the delay of scanning and then reading the neural spike signals. Since the conditional process of 324 allocates a predetermined allocation of J' and K' groups, process 326 allows a user to vary the designation of the J' and K' groups based on further observation of the neural activity.

In the embodiment depicted in FIG. 3B, if the neural activity conditions are determined to be between process 316 and 322, i.e., a range of S, where x'≤S≤x", then the operation follows that of FIG. 3A (see Label B). As such, according to the above examples, if the neural activity conditions indicate that S=3, 4, or 5, x'=3, and x"=5, then x'≤S≤x" is satisfied and no division of the M groups into read and scan mode groups is carried out. Thus, the operation returns to that of FIG. 3A, as indicated by label B. In essence, the exemplary threshold of process 316 is for capturing relatively smaller regions of neural activity on a continuous basis, while conversely, the threshold of process 322 is for capturing relatively larger regions of neural activity on a continuous basis. Thus, between these threshold limits, as described in relation to FIG. 2A, the operation is governed by a scan mode followed by a read mode that responds to the results of the scan mode.

Figure 3C:
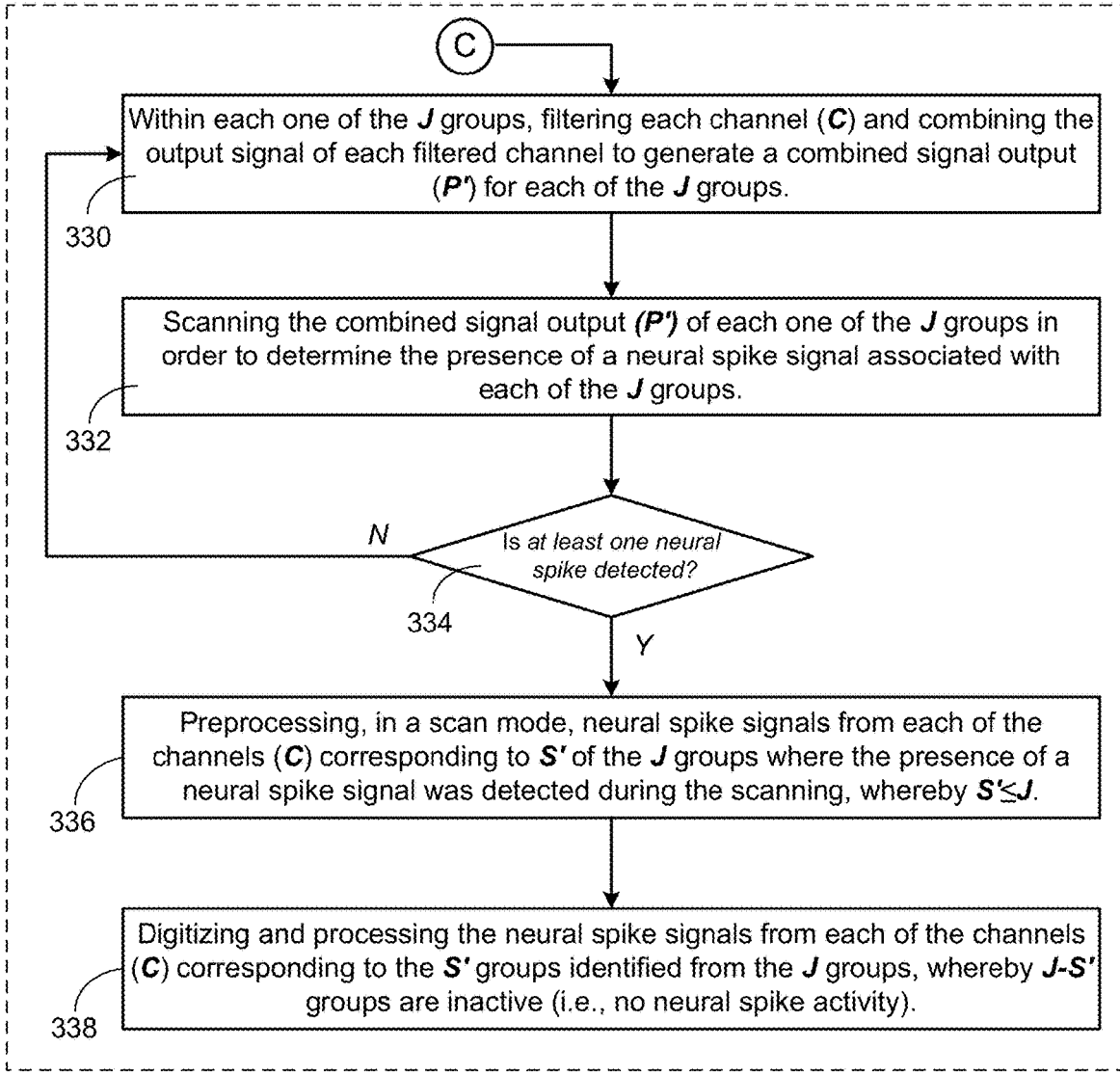
Figure 3C:
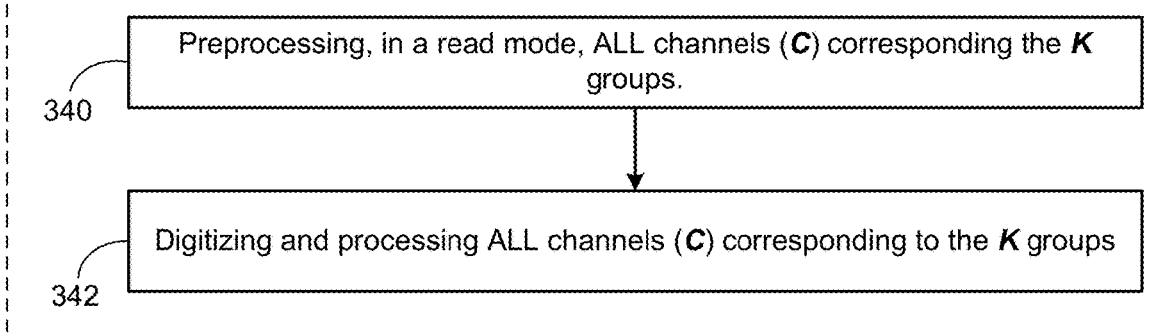

FIG. 3C shows the process steps of providing an embodiment for simultaneously scanning and reading neural signal activity on the electrodes, once electrode groups J and K have been designated based on satisfying threshold condition 316 illustrated in FIG. 3B. Processes 330-338 thus correspond to a scan mode of operation for the electrodes of group J, while processes 340-342 are associated with simultaneously reading group K electrodes during the scanning of group J.

At 330, within each one of the J groups, a combined signal output (P') for each of the J groups is generated by filtering each channel (C) and combining the output signal of each filtered channel. For example, for J=61 groups applying to Group 4-Group 64, '61' of the signal combining circuits 202a-202m (FIG. 2) generate combined outputs O/P$_4$-O/P$_m$. (FIG. 2), respectively.

At 332, the combined signal output (P') of each one of the J groups are scanned in order to determine the presence of a neural spike signal associated with each of the J groups. For example, the combined outputs O/P$_4$-O/P$_m$. (FIG. 2) from the J=61 groups are scanned using '61' of the neural signal detection circuits 210a-210m (FIG. 2) in order to determine the presence of one or more neural spike signals on each of the outputs O/P$_4$-O/P$_m$. (FIG. 2).

At 334, it is determined whether at least one neural spike signal is detected during the scanning (332) of, for example, outputs O/P$_4$-O/P$_m$. (FIG. 2). If no neural spike signal is detected, the process returns to 330. However, if at least one neural spike signal is detected from S' of the J groups, at 336 neural spike signals from each of the channels (C) corresponding to the S' groups where the presence of one or more neural spike signals were detected during the scanning are preprocessed (e.g., filtered and amplified). For example, if S'=3 (e.g., Group 4-Group 6) of the J=61 groups indicate the presence of one or more neural spike signals from outputs O/P$_4$-O/P$_6$ (FIG. 2), then neural spike signals from each of the channels (e.g., 1 . . . C=8) corresponding to these S' groups (e.g., Group 4-Group 6) are preprocessed (e.g., filtered and amplified) using twenty-four (C=8×S'=3=24) of the neural signal detection circuits 210a-210m (FIG. 2).

At 338, the neural spike signals of the S' groups (e.g., Group 4-Group 6) that are preprocessed (e.g., filtered and amplified) using twenty-four of the neural signal detection circuits 210a-210m (FIG. 2) are then digitized by the A/D conversion units within these three neural signal detection circuits. Following this conversion, other processing may occur such as, but not limited, storing the digitized neural spike signals detected from all the channels of the S' groups (e.g., Group 4-Group 6). According to other processing, the digitized neural spike signals may be packetized for WiFi, Bluetooth, or other radio transmission.

While the above processes 330-338 are performing, at 340 and 342, the read mode of operation occurs simultaneously. More particularly, at 340, all the channels (e.g., 1 . . . C=8) corresponding to each of the K groups are preprocessed (e.g., filtered and amplified). For example, for K=3 (Group 1-Group 3) of the M=64 groups, all of the channels (C) corresponding to each of the K groups (Group 1-Group 3) are preprocessed (e.g., filtered and amplified) using another twenty-four (C=8×K=3=24) of the neural signal detection circuits 210a-210m (FIG. 2).

At 342, following the preprocessing (340), all of the channels (C) corresponding to each of the K groups (Group 1-Group 3) are then digitized by the A/D conversion units within the twenty-four (C=8×K=3=24) of the neural signal detection circuits 210a-210m (FIG. 2) utilized in process 340. Following this digital conversion process, other processing may occur such as, but not limited to, storing the digitized neural spike signals detected from all the channels of the K groups (e.g., Group 1-Group 3). According to other processing, the digitized neural spike signals may be packetized for WiFi, Bluetooth, or other radio type transmissions.

Figure 3D:
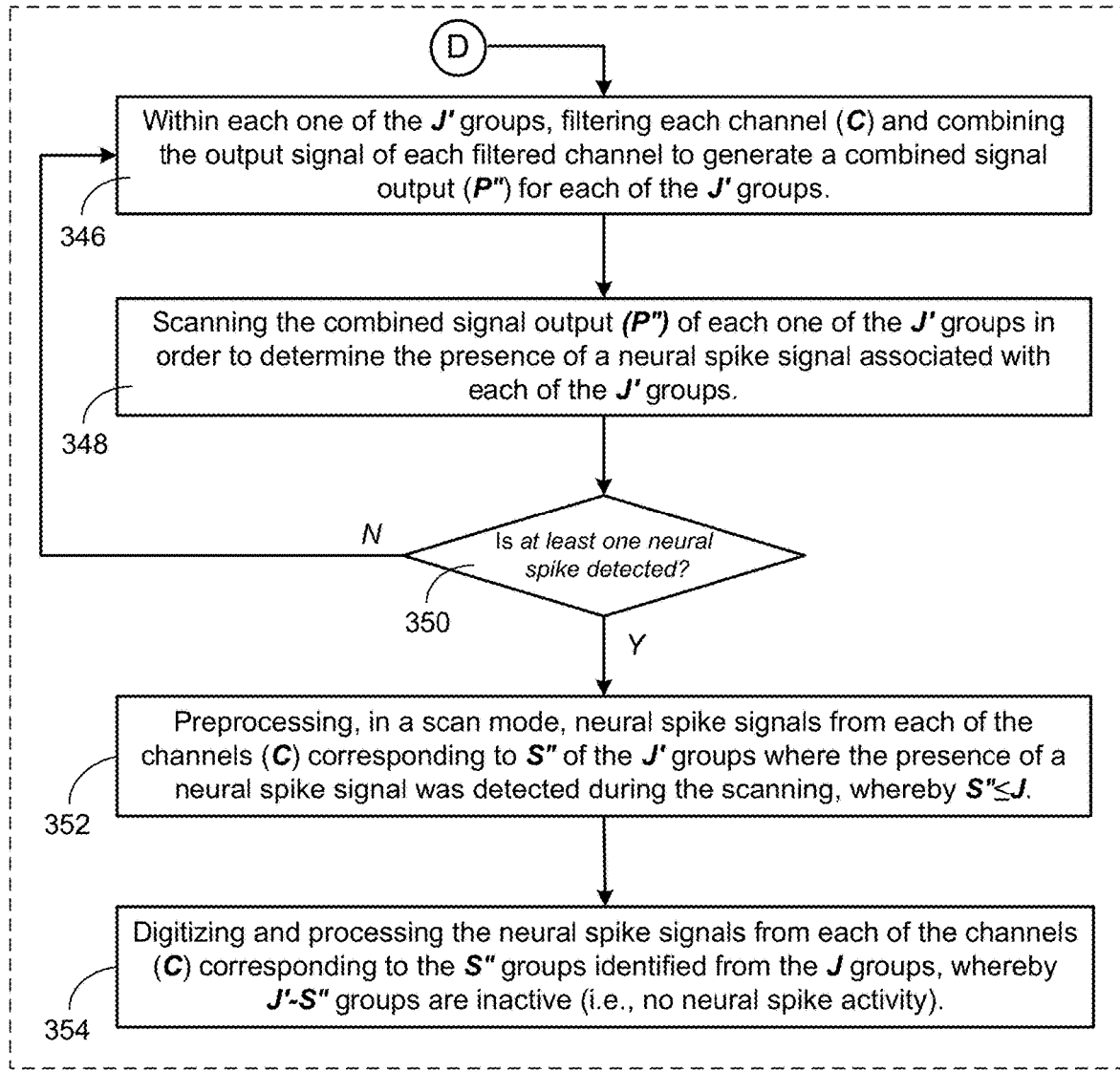
Figure 3D:
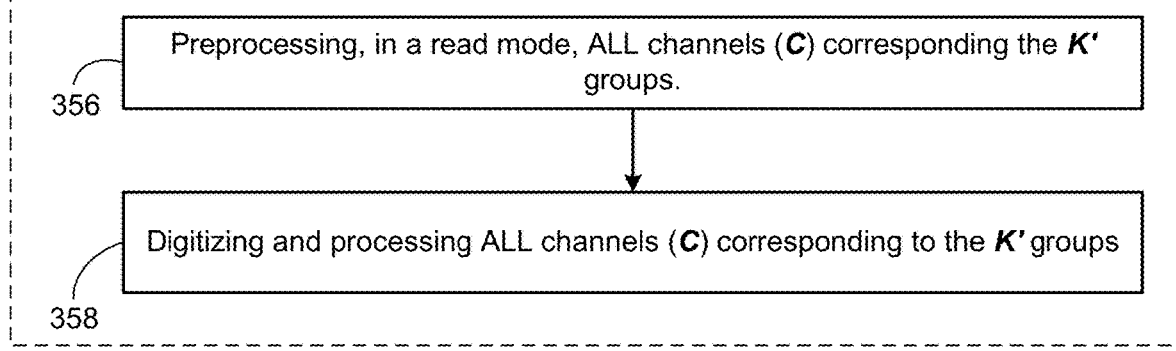

FIG. 3D shows the process steps of providing an embodiment for simultaneously scanning and reading neural signal activity on the electrodes, once electrode groups J' and K' have been designated based on satisfying threshold condition 322 illustrated in FIG. 3B. Processes 346-354 thus correspond to a scan mode of operation for the electrodes of group J', while processes 356-358 are associated with simultaneously reading group K' electrodes during the scanning of group J'.

At 346, within each one of the J' groups, a combined signal output (P''') for each of the J' groups is generated by filtering each channel (C) and combining the output signal of each filtered channel. For example, for J'=58 groups applying to Group 7-Group 64, '58' of the signal combining circuits 202a-202m (FIG. 2) generate combined outputs O/P$_7$-O/P$_m$. (FIG. 2), respectively.

At 348, the combined signal output (P''') of each one of the J groups are scanned in order to determine the presence of a neural spike signal associated with each of the J groups. For example, the combined outputs O/P$_7$-O/P$_m$. (FIG. 2) from the J'=58 groups are scanned using '58' of the neural signal detection circuits 210a-210m (FIG. 2) in order to determine the presence of one or more neural spike signals on each of the outputs O/P$_7$-O/P$_m$. (FIG. 2).

At 350, it is determined whether at least one neural spike signal is detected during the scanning (332) of, for example, outputs O/P$_7$-O/P$_m$. (FIG. 2). If no neural spike signal is detected, the process returns to 346. However, if at least one neural spike signal is detected from S" of the J' groups, at 352 neural spike signals from each of the channels (C) corresponding to the S" groups where the presence of one or more neural spike signals were detected during the scanning are preprocessed (e.g., filtered and amplified). For example, if S"=2 (e.g., Group 7-Group 8) of the J'=58 groups indicate the presence of one or more neural spike signals from outputs O/P$_7$-O/P$_8$ (FIG. 2), then neural spike signals from each of the channels (e.g., 1 ... C=8) corresponding to these S" groups (e.g., Group 7-Group 8) are preprocessed (e.g., filtered and amplified) using sixteen (C=8×S"=2=16) of the neural signal detection circuits 210a-210m (FIG. 2).

At 352, the neural spike signals of the S" groups (e.g., Group 7-Group 8) that are preprocessed (e.g., filtered and amplified) using sixteen of the neural signal detection circuits 210a-210m (FIG. 2) are then digitized by the A/D conversion units within these three neural signal detection circuits. Following this conversion, other processing may occur such as, but not limited, storing the digitized neural spike signals detected from all the channels of the S" groups (e.g., Group 7-Group 8). According to other processing, the digitized neural spike signals may be packetized for WiFi, Bluetooth, or other radio transmission.

While the above processes 346-354 are performing, at 356 and 358, the read mode of operation occurs simultaneously. More particularly, at 356, all the channels (e.g., 1 ... C=8) corresponding to each of the K' groups are preprocessed (e.g., filtered and amplified). For example, for K'=6 (Group 1-Group 6) of the M=64 groups, all of the channels (C) corresponding to each of the K' groups (Group 1-Group 6) are preprocessed (e.g., filtered and amplified) using another 40 (C=8×K'=6=48) of the neural signal detection circuits 210a-210m (FIG. 2).

At 358, following the preprocessing (356), all of the channels (C) corresponding to each of the K' groups (Group 1-Group 6) are then digitized by the A/D conversion units within the forty (C=8×K'=6=48) of the neural signal detection circuits 210a-210m (FIG. 2) utilized in process 356. Following this digital conversion process, other processing may occur such as, but not limited to, storing the digitized neural spike signals detected from all the channels of the K' groups (e.g., Group 1-Group 6). According to other processing, the digitized neural spike signals may be packetized for WiFi, Bluetooth, or other radio type transmissions.

In the above exemplary embodiments, the allocation of groups for simultaneous read mode and scan mode operations (e.g., FIG. 3C, FIG. 3D) can be configured based on detected neural spike signal activities. In other embodiments, however, the allocation of groups for simultaneous read mode and scan mode operations can be responsive to which groups, and thus what area or areas of the brain, is exhibiting neural spike signal activity.

Figure 4:
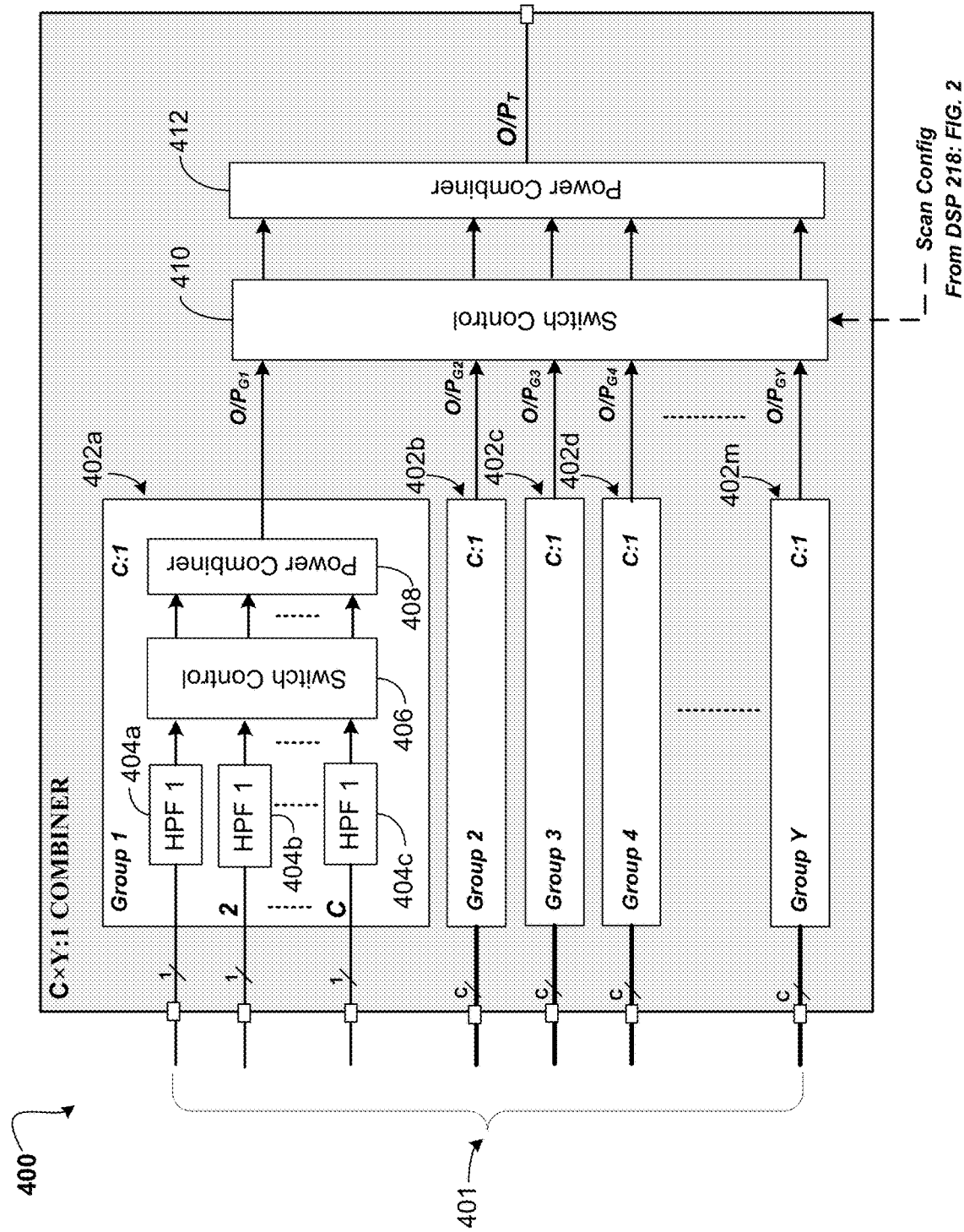
FIG. 4 is a neural signal combining circuit associated with FIG. 2's neural recording system, according to one exemplary embodiment.

Referring to FIG. 4, an exemplary embodiment of a signal combining circuit 400 is illustrated. Signal combining circuit 400 can be used to implement each of the plurality of M signal combining circuits 202a-202m within the neural recording device 200 of FIG. 2. The circuit 400 includes a plurality of signal combining circuits 402a-402m, a switch control unit 410, and a final stage power combiner unit 412. The plurality of signal combining circuits 402a-402m can each include a plurality of high pass filters 404a-404c, a switch control unit 406, and a power combiner unit 408.

When neural signals are detected by the N electrodes 110 (FIG. 1), the neural signals are received by the plurality of inputs 401, whereby each input from the plurality of inputs 401 is coupled in series to a high pass filter in the respective signal combining circuits 402a-402m. For example, within signal combining circuit 402a, inputs 1 to C are each coupled in series with high pass filters 404a-404c. Similarly, within each of the other signal combining circuits 402b-402m, inputs 1 to C are each coupled in series with the high pass filters within those signal combining circuits 402b-402m.

Each high pass filter associated with signal combining circuits 402a-402m is configured to output high-frequency signals (i.e. neural spikes), which may then be passed to their respective switch control units. For example, within signal combining circuit 402a, high-frequency signals (i.e. neural spikes) passed through high pass filters 404a-404c may then be passed to switch control unit 406. When neural spike signals are received by switch control unit 406, the neural spike signals may then be passed onto power combiner unit 408 when a corresponding switch within the switch control unit 406 is actuated to a closed circuit position (i.e., enabled).

The high pass filters, switch control units, and power combiner units associated with the other signal combining circuits 402b-402m are identical to signal combining circuit 402a, and thus operate in the same manner. Accordingly, within each of the signal combining circuits 402a-402m, filtered neural spike signals received from inputs or channels 1 to C are combined by respective power combiner units and output to switch control unit 410. Switch control unit 410 then receives one or more combined neural spike signals that are output from each of the signal combining circuits 402a-402m. Subsequently, switch control unit 410 controls the transmission of the combined neural spike signals to power combiner 412, whereby under the control of switch control unit 410, the output of any one or more of the signal combining circuits 402a-402m can be further combined at the output O/P$_T$ of power combiner 412.

More specifically, the combined output O/P$_{G1}$ from signal combining circuit 402a may be transmitted to power combiner 412 under the control of switch control unit 410, the combined output O/P$_{G2}$ from signal combining circuit 402b may be transmitted to power combiner 412 under the control of switch control unit 410, the combined output O/P$_{G3}$ from signal combining circuit 402c may be transmitted to power combiner 412 under the control of switch control unit 410, the combined output O/P$_{G4}$ from signal combining circuit 402d may be transmitted to power combiner 412 under the control of switch control unit 410, etc., until finally the combined output O/P$_{GY}$ from signal combining circuit 402m may be transmitted to power combiner 412 under the control of switch control unit 410. Thus any combination of these outputs O/P$_{G1}$-O/P$_{GY}$ can be combined at the output O/P$_T$ of the final stage power combiner 412 using the final stage switch control unit 410. As such, DSP 218 (FIG. 2) may generate a configuration signal that enables the predetermined combining of any combination of outputs O/P$_{G1}$-O/P$_{GY}$.

Accordingly, scanning for neural spike signals within a given area of the brain cortex can be adjusted to be more or less coarse by configuring the number of outputs from the respective signal combining circuits 402a-402m that are combined. For example, in one implementation, signal combining circuit 400 can be incorporated within signal combining circuit 202a (FIG. 2) or any other one or more of the other signal combining circuits 202b-202m (FIG. 2) of the neural recording device 200 of FIG. 2. As such, according to a first example configuration, switch control unit 410 may be programmed to only enable the output O/P$_{G1}$ of signal combining circuit 402a to be sent to the power combiner 412 and thus provide the output O/P$_T$ of circuit 400. Since in the given example, the only output received by the power combiner 412 is output O/P$_{G1}$ from signal combining circuit 402a, the power combiner 412 has no other signal or signals to combine at its output O/P$_T$. Thus, the first configuration can be utilized to generate a single output (i.e., one of O/P$_{G1}$-O/P$_{GY}$) from one of the plurality of signal combining circuits 402a-402m of circuit 400. Configured in this manner, circuit 400 facilitates the operation of the signal combining circuits 202a-202m of FIG. 2, whereby, for example, signal combining circuit 402a is used to scan neural spike signal activities within region r1 (FIG. 1) of the cortex 110 (FIG. 1).

Alternatively, according to a second example configuration, switch control unit 410 may be programmed to enable both the output O/P$_{G1}$ of signal combining circuit 402a and the output O/P$_{G2}$ of signal combining circuit 402b to be sent to the power combiner 412 for generating the output O/P$_T$ of circuit 400. Here, outputs O/P$_{G1}$ and O/P$_{G2}$ are received and combined by the power combiner 412 to form the combined output O/P$_T$ of circuit 400. Configured in this manner, circuit 400 facilitates an alternative operation of the signal combining circuits 202a-202m of FIG. 2, whereby, for example, signal combining circuits 402a and 402b are used to scan neural spike signal activities within larger region r'1 (FIG. 1) of the cortex 110 (FIG. 1). Thus, a single signal combining circuit 402a can be used to scan for neural spike signal activity over an increase area of the cortex. This configuration may be utilized in scenarios where there is reduced neural spike signal activity over a given area of the cortex and, therefore, signal processing efficiency is facilitated by monitoring a larger group of electrodes. Using FIG. 4 within the embodiment of FIG. 2, some of the of M outputs (FIG. 2) include a combination of more of the N inputs, while other ones of the M outputs include an aggregation of less of the N inputs. For example, in this second example configuration, signal combining circuit 202a may use circuit 400, whereby signal combining circuits 402a and 402b combine 2C (e.g., 2C=2*8=16 electrodes) electrodes, while the remaining signal combining circuit 202b-202m may aggregate a lesser number of C/F (e.g., C/F=8/2=4 electrodes) electrodes.

The larger group configurations enable the use of a reduced number of neural signal detection circuits, thus contributing to power consumption savings facilitated by turning off unused neural signal detection circuits. In the above example implementation where circuit 400 is used in neural recording device 200 (FIG. 2), by virtue of signal combining circuits 402a and 402b being used to scan neural spike signal activities over a larger region r'1 (FIG. 1) of the cortex 110 (FIG. 1), a single neural signal detection circuit such as neural signal detection circuit 210a may be utilized. Consequently, neural signal detection circuit 210b may be switched off.

Figure 5:
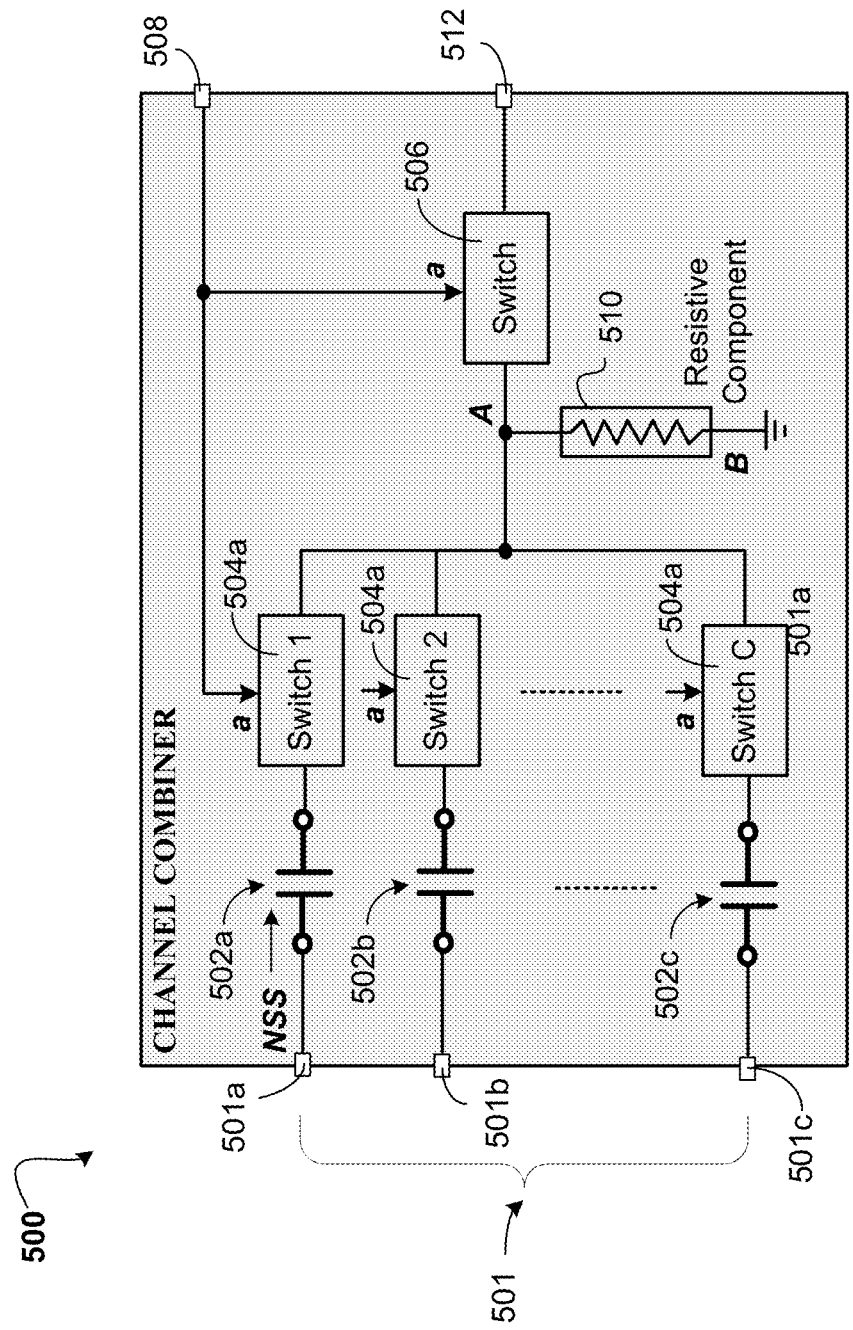
FIG. 5 shows another neural signal combining circuit associated with FIG. 2's neural recording system, according to another exemplary embodiment.

Referring to FIG. 5, an exemplary embodiment of a signal combining circuit 500 is shown. Signal combining circuit 500 can be used to implement each of the plurality of M signal combining circuits 202a-202m within the neural recording device 200 of FIG. 2. Moreover, the exemplary embodiment of signal combining circuit 500 can be used to implement each of the signal combining circuits 402a-402m (FIG. 4) within signal combining circuit 400 (FIG. 4). The circuit 500 can include a plurality of capacitors 502a-502c, input switches 504a-504c, a resistive unit 510, and an output switch 506. As depicted, the capacitors 502a-502c are respectively in series with input switches 504a-504c. In particular, capacitor 502a is coupled in series with switch 504a, capacitor 502b is coupled in series with switch 504b, etc., until finally capacitor 502c is coupled in series with switch 504c. The output of each of the switches 504a-504c are electrically coupled to both switch 506 and resistive unit 510, as indicated at A. In addition to the resistive unit 510 being coupled to the output of switches 504a-504c, resistive unit 510 is also connected to ground, as indicated at B. While one end of output switch 506 is coupled to both the switches 504a-504c and the resistive unit 510, the other end of the output switch 506 forms the output 512 of the channel combiner circuit 500. As illustrated, the output switch 506 and switches 504a-504c are controlled (e.g., enabled/disabled) via a scan enable signal received from input 508, as indicated by a.

When a scan enable signal is received at input 508, upon actuation of the switches 504a-504c, 506 to a closed circuit, the combination of each of series capacitors 502a-502c and the resistive unit 510 forms a high pass filter for each of the signals received from inputs 501.

Accordingly, only high-frequency signals (i.e. neural spikes) are passed through each of series capacitors 502a-502c and resistive unit 510. For example, a neural spike signal NSS received at input 501a is passed through the high-pass filter formed by capacitor 502a and resistive unit 510, while other signals outside the frequency band of this filter are attenuated. It may be appreciated that since neural spike signals range from 100s of Hz to several kHz, the resistive unit 510 may need a large resistance value (e.g. 100s of Mega-Ohms or more) to accomplish the requisite filtering. The resistive unit 510 can thus be implemented with transistor-based pseudo resistors capable of generating a higher resistance per chip area compared to fabricating, for example, passive resistive components.

Signals are generated based on different voltages generated by the resistive unit 510 based on the neural spike signals received from inputs 501. Accordingly, as neural spike signals are received by more inputs, an increase in voltage is generated by the resistive unit 510 at A. For example, if neural spike signals are received at input 501a, a voltage $V_1$ is generated. However, if neural spike signals are received at inputs 501a, 501b, and 501c, an increased current from these aggregate neural spike signal generates a voltage $V_2$, whereby $V_2 > V_1$. Thus, different voltage levels are generated as a function of the combined neural spike signals received from inputs 501.

Figure 6:
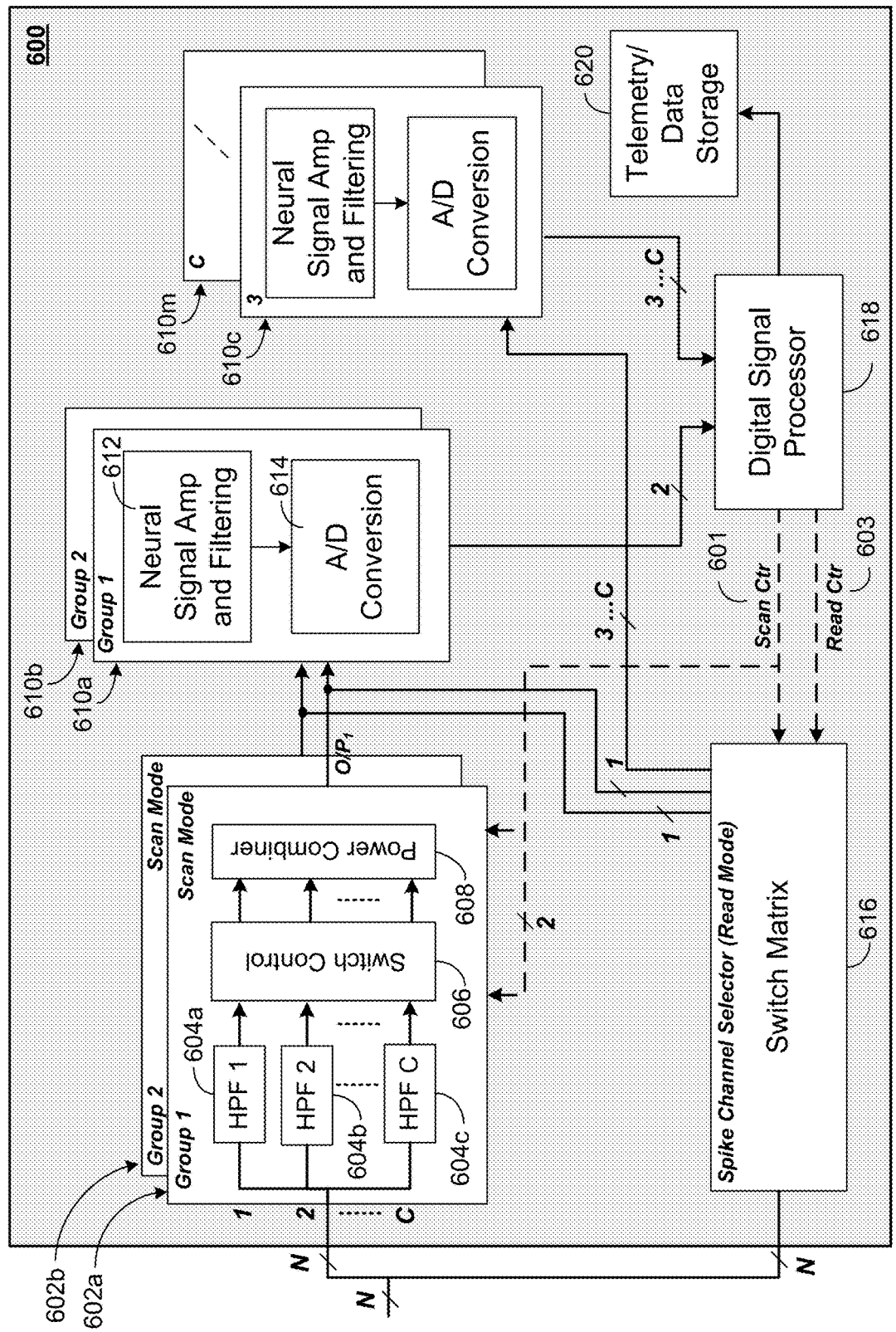
FIG. 6 shows another neural recording device associated with FIG. 1's system for monitoring neurological brain activity, according to another exemplary embodiment.

FIG. 6 shows another neural recording system 600 associated with FIG. 1's system for monitoring neurological brain activity, according to another exemplary embodiment. The various components of neural recording system 600 are identical to, and operate in the same or similar manner with, the neural recording system 200 of FIG. 2. In contrast to the embodiment of FIG. 2, however, two (2) signal combining circuits 602a-602b are coupled to two (2) neural signal detection circuits 610a-610b, while a plurality of other (3 . . . C) neural signal detection circuits 610c-610m are coupled directly to the switch matrix 616 output without being utilized in the scan mode operation.

The neural recording device 600 includes both scan mode and read mode circuits for detecting and recording neural spike signals associated with a subject's brain (e.g., FIG. 1: cortex region 120). The scan mode and read mode circuits may contemplate using separate devices or circuits to provide the scan mode and read mode operations. Alternatively, however, the scan mode and read mode circuits may contemplate using common/shared devices or circuits during the scan mode and read mode operations.

The scan mode circuit detects neural spike activity within any of the two (2) groups of electrodes selected from a total of N electrodes that are coupled to the brain. Accordingly, the total of N electrodes that are coupled to the brain are divided into two (2) symmetric groups, whereby each of the two (2) groups have C electrodes for detection, such that, N=2C. Alternatively, the total of N electrodes that are coupled to the brain are divided into two (2) asymmetric groups, where each of the two (2) groups have different electrode numbers (e.g., Group 1=D electrodes; Group 2=E electrodes) for detection, such that, N=D+E.

The scan mode circuit includes signal combining circuits 602a-602b that each detect the occurrence of one or more neural spike signals occurring within a corresponding group of electrodes taken from the total of N electrodes coupled to the brain. For example, signal combining circuit 602a detects the occurrence of one or more neural spike signals occurring within the first group (i.e., Group 1) of 1 to C electrodes, and signal combining circuit 602b detects the occurrence of one or more neural spike signals occurring within the second group (i.e., Group 2) of other 1 to C electrodes.

Each of the signal combining circuits 602a-602b aggregate the signals received from respective input electrodes 1 to C. For example, signal combining circuit 602a includes high-pass filters 604a-604c, a switch control unit 606, and a power combiner 608. Accordingly, signals received from input electrodes 1 to C are each filtered in order to pass the higher frequency neural spike signals, while filtering other spurious unwanted signals. The filtered outputs from the high-pass filters 604a-604c are coupled to the switch control unit 606, which enables or inhibits the transmission of the filtered outputs to the power combiner 608. The power combiner 608 may then couple any of the neural spikes signals received from high-pass filters 604a-604c to a single output $O/P_1$. The power combiner 608 output $O/P_1$ thus enables the aggregation of any neural spike activity within the group of 1 to C electrodes regardless of whether only a single neural spike signal is received (e.g., neural spike received from only electrode 1), a few neural spike signals are received (e.g., neural spikes received from electrodes 1, 3, and 6), or all the neural spike signals are received (e.g., neural spikes received from electrodes 1 to C). Signal combining circuit 602b may also include the same or similar high-pass filters, switch control units, and power combiners to that of signal combining circuit 602a described above.

According to alternative non-limiting implementations, the signal combining circuits 602a-602b may each receive a different number of input electrodes. For example, while combining circuit 602a receives input electrodes 1 to C (e.g., electrodes 1-32), combining circuit 602b can receive input electrodes 1 to C' (e.g., electrodes 1-64). In this asymmetric mapping of input electrodes (i.e., 1-N), more electrodes (e.g., electrodes 1-64) may be assigned to a combining circuit for a given area $A_r$ of the cortex where less neurological signal activity is expected. Conversely, less electrodes (e.g., electrodes 1-32) may be assigned to a combining circuit for the same give area $A_r$ of the cortex where more neurological signal activity is expected. Thus, the assignment of electrodes to combining circuits can be determined based on neural signal detection granularity requirements.

The scan mode circuit may also include a plurality of M neural signal detection circuits 610a-610m, some of which (i.e., 610a-610b) are each coupled to a respective one of the signal combining circuits (i.e., 602a-602b), while others (i.e., 610c-610m) are coupled directly to the switch matrix for the read-mode operation.

For example, since this embodiment detects neural signal activity from two groups of electrodes (i.e., Group 1 & Group 2), neural signal detection circuit 610a is coupled to signal combining circuit 602a, while neural signal detection circuit 610b is coupled to signal combining circuit 602b. Thus, neural signal detection circuit 610a detects the occurrence of any neural spike signals output from signal combining circuit 602a, while neural signal detection circuit 610b detects the occurrence of any neural spike signals output from signal combining circuit 602b.

Each of the plurality of neural signal detection circuits 610a-610m may include a filtering and signal amplification circuit 612 and an analog-to-digital (A/D) convertor circuit 614 coupled to the filtering and signal amplification circuit 612. The filtering and signal amplification circuit 612 may include a bandpass filter that is configured to pass a range of frequency components corresponding to the presence of neural spike signals, while suppressing other unwanted spurious signals (e.g., noise). Any neural spike signals passed by the bandpass filter are then amplified by an amplifier circuit prior to being coupled to and received by the analog-to-digital (A/D) convertor circuit 614. At the analog-to-digital (A/D) convertor circuit 614, any filtered and amplified neural spike signals are converted to digitized neural spike signals. Thus, detected neural spike signals are converted into a digital format for facilitating read/scan mode operations of the neural recording device 600. Accordingly, during the read mode, one or more neural spike signals present on all of the 1 to C electrodes associated with either one of the two (2) groups are recorded for further neurologically-related analysis, as described in more detail in the following paragraphs.

In some embodiments, the analog-to-digital (A/D) convertor circuit 614 may contemplate the use of a digital threshold comparison capability, whereby the digitized signals are compared with a digital threshold value in order to ensure that neural spikes, and not an unwanted signal components, have been detected and digitized. In other embodiments, such a digital threshold comparison capability can be incorporated within other circuitry/devices (e.g., DSP 618) associated with the neural recording device 600.

The read mode circuit records all neural spike signals present within any one of the two groups (i.e., Group 1 or Group 2) of electrodes where neural spike activity is detected by the scan mode circuit. In particular, when a neural spike signal is detected on at least one of the electrodes within one of the two groups of electrodes (e.g., Group 1), all of the electrodes within that group are routed through for signal recordation. Accordingly, routing and signal recordation (e.g., digitization, formatting, storage, etc.) is applied to one of the two groups (e.g., Group 1) where neural signals are detected, while signal routing and recordation is suspended for the other group (e.g., Group 2) within the two (2) groups with no detected neural signal activity. Thus, routing and recordation of neural signals from the N electrodes (i.e., N=2C) can be achieved using a reduced number of C channels (e.g., 50% reduction).

The read mode circuit may include a switch matrix 616 and a digital signal processor (DSP) 618. The read mode circuit may additionally include a telemetry and data storage unit 620. As depicted, the N electrodes coupled to the brain are also received as inputs to the switch matrix 616. However, from the N inputs, the switch matrix 616 has a reduced number outputs (e.g., 1 to C) that are also coupled to the plurality of neural signal detection circuits 610a-610m, some of which (i.e., 610a-610b) are associated with the scan mode circuit. As such, the illustrated exemplary embodiment includes a first circuit/device/component (i.e., neural signal detection circuits 210a-210b) that can form part of both the read mode circuit and the scan mode circuit, while a second circuit/device/component (i.e., neural signal detection circuits 210c-210m) is part of the read mode circuit. It should however be appreciated that the 3-C outputs of the switch matrix 616 are coupled to neural signal detection circuits 610c-610m that operate in a similar or identical manner to that of neural signal detection circuits 610a-610b. As previously described, any neural spike signals routed to the 1-C outputs of the switch matrix 216 are filtered, amplified, and digitized (i.e., front end processing) by a respective one of the plurality of 1-C neural signal detection circuits 610a-610m.

The DSP 618 may include any circuit capable of processing digital signals (e.g., neural signals, etc.) and generating commands for the execution of the neural recording device 600 operability. In particular, the DSP 618 may initiate, via a read control signal 603, the routing operation of the switch matrix 616 based on the scan circuit detecting which groups of the two groups are exhibiting neural switch activity. Moreover, the DSP 618 may activate and deactivate the operation of the signal combining circuits 602a-602b and consequently the scan control circuit, via a scan control signal 601. Once the routing operation of the switch matrix 616 is initiated, neural signals routed to switch outputs 1-C are detected and sent to the DSP 618 from the neural signal detection circuits 610a-610m. For example, if neural spike activity is detected on only signal combining circuit 602a (Group 1), the signals associated with the 1 to C electrodes coupled to combining circuit 602a is routed to the switch matrix 616 output 1-C. Using a numerical example, if 8 electrodes (i.e., C=8) are coupled to circuit 602a, then 8 electrodes corresponding to the input of combining circuit 202a are routed to 8 outputs of the switch's 616 outputs. These 8 outputs are then processed by 8 neural signal detection circuits, whereby the processed outputs from these 8 neural signal detection circuits are received and recorded by the DSP 618.

The recording process may include storing the neural spike digital values of the routed 1 to C electrodes corresponding to the one of the signal combining circuits that exhibited neural spike activity during the scan mode. Using the above example, during the recording process, the DSP 616 stores the digital values associated with any of the neural spike signals detected on the 8 input electrodes of combining circuit 602a. The DSP 618 may store the neural spike digital values either within memory located on the DSP 618, or alternatively, the DSP 618 may forward this data to the data storage and telemetry unit 620. The recording process may also include storing additional information associated with each of the neural spike digital values. For example, data corresponding to each neural signal's time/date of recording (e.g., Mar. 31, 2016 at 10:30 AM) and electrode number (e.g., electrode #1006) may be stored with each of the neural spike digital values.

According to some embodiments, the stored data corresponding to each neural signal's time/date of recording (e.g., Mar. 31, 2016 at 10:30 AM), electrode number (e.g., electrode #1006), and digital value may be transmitted via the telemetry functionality of unit 620. In other embodiments, the DSP 618 may include an embedded transceiver circuit, whereby the stored data corresponding to each neural signal's time/date of recording (e.g., Mar. 31, 2016 at 10:30 AM), electrode number (e.g., electrode #1006), and digital value may be transmitted using such a transceiver. According to yet another embodiment, both the telemetry/data storage unit 620 and the DSP's 618 transceiver can provide simultaneous transmission means for, among other things, the each neural signal's time/date of recording (e.g., Mar. 31, 2016 at 10:30 AM), electrode number (e.g., electrode #1006), and digital value. In such an embodiment, the throughput of neural spike data transmitted from the neural recording device 600 to the external unit 102 (FIG. 1) can be dynamically increased to facilitate real-time monitoring of neurological activity.

Although the scan mode and read mode circuits have been described using the exemplary embodiment of neural recording device 600, it will be appreciated that such functionality can be implemented using alternative hardware, software, firmware, or any combination thereof. Exemplary neural recording device 600 is an alternative embodiment, where the received electrodes are split into two groups as opposed to three or more groups, as with neural recording device 200 (FIG. 2). Since each of the signal combining circuits can include more than two inputs (e.g., 128 electrodes), for signal recording purposes, more than two signal detection circuits (e.g., 128 detection circuits) are utilized. As such, two (2) detection circuits coupled to the two signal combining circuits are used along with an additional hundred and twenty-six (126) detection circuits dedicated for the signal recording.

Figure 7:
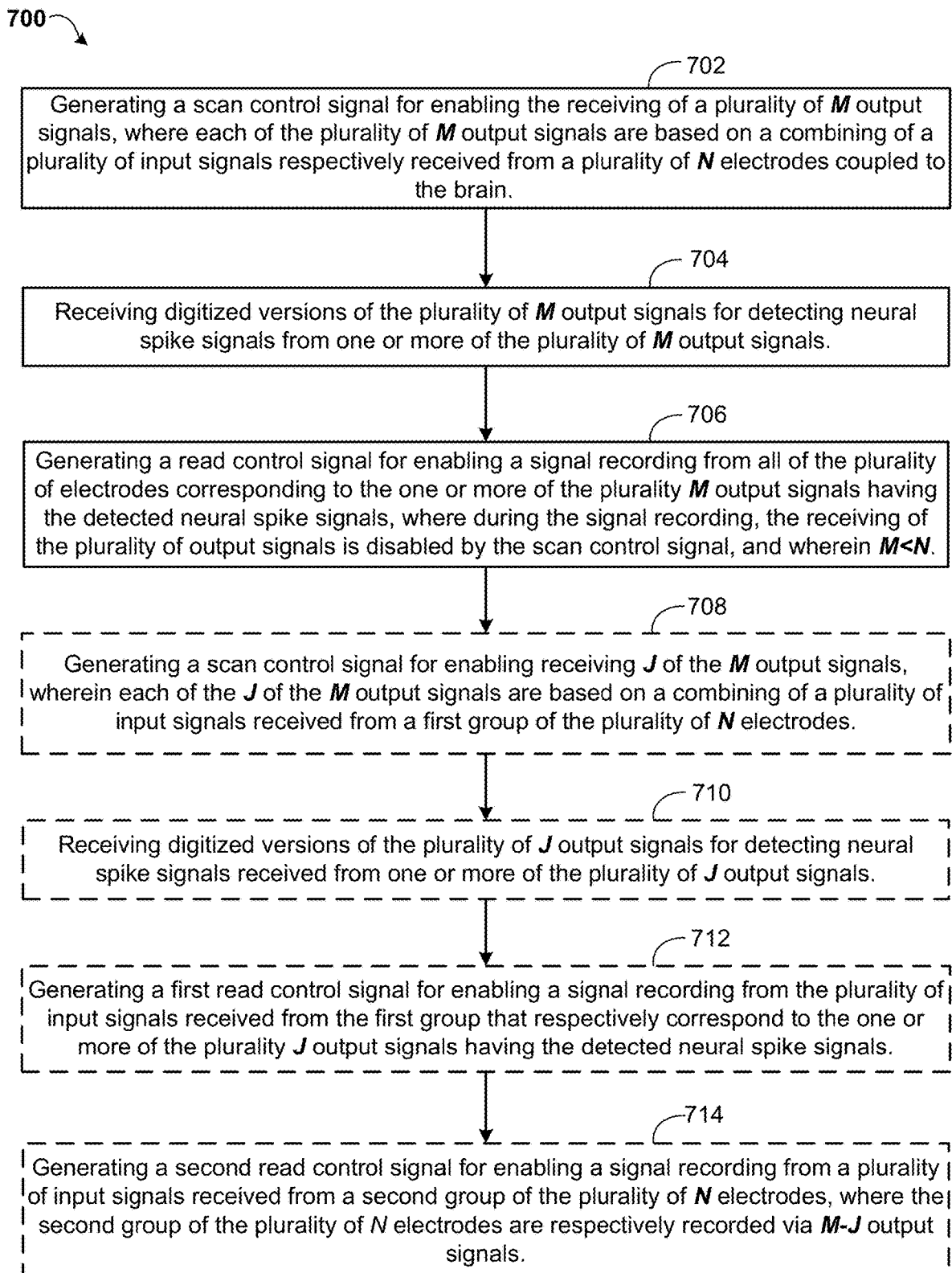
FIG. 7 is a flow diagram associated with the scan-mode and read-mode controlling of a neural recording device, according to one exemplary embodiment.

FIG. 7 is a flow diagram 700 associated with controlling the scan-mode and read-mode processes of a neural recording system, according to one exemplary embodiment. The corresponding processes of flow diagram 700 may be executed as a Neural Signal Recording Control (NSRC) program on any processing device, such as, for example, DSP 218 (FIG. 2) or DSP 618 (FIG. 6). FIG. 7 is described with the aid of the exemplary embodiment of FIG. 2.

At 702, a scan control signal for enabling the receiving of a plurality of M output signals is generated, where each of the plurality of M output signals are based on a combining of a plurality of input signals (i.e., signal groups) respectively received from a plurality of N electrodes coupled to the brain. For example, a Scan Ctr signal 201, which is output from DSP 218, enables the switch control units 206 within each of the plurality of M signal combining circuits 202a-202m (Groups 1-M) by actuating them to a closed position. This switch enabling function allows the outputs $O/P_1$-$O/P_m$ of the plurality of M signal combining circuits 202a-202m (Groups 1-M) to be coupled to the plurality of M neural signal detection circuits 210a-210m for the scan mode operation.

At 704, digitized versions of the plurality of M output signals are received for detecting neural spike signals from one or more of the plurality of M output signals. For example, the plurality of M neural signal detection circuits 210a-210m pre-process (e.g., amplify and filter) and digitize any neural spike signals that are received from the respective outputs $O/P_1$-$O/P_m$ of the plurality of M signal combining circuits 202a-202m (Groups 1-M).

At 706, a read control signal is generated for enabling the recording of neural spike signals received from all of the plurality of electrodes (i.e., signal groups) corresponding to any one or more of the plurality M output signals having detected neural spike signals. During the signal recording mode, the scan mode receiving of the plurality of output signals is disabled by the scan control signal. For example, a Read Ctr signal 203, which is output from DSP 218, enables the switch matrix 216 to route all of the input signals associated with the one or more plurality of M signal combining circuits 202a-202m (Groups 1-M) having the detected neural spike signals. Based on this Read Ctr signal 203, for instance, if signal combining circuits 202a and 202b have detected neural signal activity at their outputs $O/P_1$-$O/P_2$, then inputs 1-C of signal combining circuit 202a and inputs 1-C of signal combining circuit 202b are subsequently routed via the switch input 231 to switch output 233. Further, during the application of the Read Ctr signal 203, the Scan Ctr signal 201 output from DSP 218 disables the switch control units 206 within each of the plurality of M signal combining circuits 202a-202m (Groups 1-M) by actuating them to an open position. This coordinated signaling between the Scan Ctr signal 201 and the Read Ctr signal 203 provides the ability to use the same plurality of M neural signal detection circuits 210a-210m during the both the scan mode and read mode operations.

As such, the number of M output signals that can be routed is less than the total number of N electrodes coupled to the brain, thus providing an increased processing efficiency caused by having less scan-mode and read-mode channels relative to the received N electrodes (i.e., input channels).

Optionally (as indicated by the dashed boxes), processes 708-714 correspond to partitioning the total of M outputs (for M groups) into J outputs (for J groups) that are scanned and then recorded based on the scanning, and M-J remaining outputs (for M-J remaining groups) that are directly recorded without any prior scanning. In order to provide a numerical example, consider M=5 total groups, whereby J=3 groups, M-J=2 groups, and each of these groups receives C=8 of the N electrodes.

As such, at 708, a scan control signal for enabling the receiving of a plurality of J output signals is generated, where each of the plurality of J output signals are based on a combining of a plurality of input signals (i.e., signal groups) respectively received from a group or subset of the plurality of N electrodes coupled to the brain. For example, a Scan Ctr signal 201, which is output from DSP 218, enables the switch control units 206 within each of the plurality of J=3 signal combining circuits 202a-202c (Groups 1-3). This switch enabling function allows the outputs $O/P_1$-$O/P_3$ of the plurality of J=3 signal combining circuits 202a-202c (Groups 1-3) to be coupled to the plurality of J=3 neural signal detection circuits 210a-210c for the scan mode operation.

At 710, digitized versions of the plurality of J output signals are received for detecting neural spike signals from one or more of the plurality of J output signals. For example, the plurality of J=3 neural signal detection circuits 210a-210c pre-process (e.g., amplify and filter) and digitize any neural spike signals that are received from the respective outputs $O/P_1$-$O/P_3$ of the plurality of J=3 signal combining circuits 202a-202c (Groups 1-3). Thus, signal activity on any one or more of the J=3 groups is determined prior to the read operation.

At 712, a first read control signal is generated for enabling the recording of neural spike signals received from all of the plurality of electrodes (i.e., signal groups) corresponding to any one or more of the plurality J output signals having the detected neural spike signals. During the signal recording, the receiving of the plurality of output signals is disabled by the scan control signal. For example, a Read Ctr1 signal 203, which is output from DSP 218, enables the switch matrix 216 to route all of the inputs associated with one or more of the plurality of J=3 signal combining circuits 202a-202c (Groups 1-3) having a detected neural spike signal based on the scan mode operation (708, 710). In response to the Read Ctr1 signal 203, if signal combining circuits 202a and 202c have been determined to include neural signal activity at their respective outputs $O/P_1$, $O/P_3$ during the scan mode (708, 710), then inputs C=8 of signal combining circuit 202a and inputs C=8 of signal combining circuit 202c are subsequently routed via the switch input 231 to switch output 233. Thus, for both the two signal combining circuits 202a, 202c having detected neural spike signal activity, a total of 16 inputs are routed via the switch input 231 to switch output 233.

At 714, a second read control signal is generated for enabling a signal recording from a plurality of input signals received from a second group or subset (M-J) of the plurality of N electrodes, where the second group of the plurality of N electrodes (i.e., M-J electrodes) are respectively recorded via M-J output signals from the switch matrix. Here, no signal combiner outputs need to be scanned since certain predetermined inputs for these signal combiners are directly routed through the switch matrix to corresponding neural signal detection circuits for subsequent recordation. For example, a Read Ctr2 signal 205, which is output from DSP 218, enables the switch matrix 216 to route the inputs corresponding to the M−J=2 predetermined signal combiner groups via the switch matrix input 231 to switch matrix output 233. Thus, for the designated inputs of the two predetermined signal combining circuits, a total of 16 inputs are routed via the switch input 231 to switch output 233.

Figure 8:
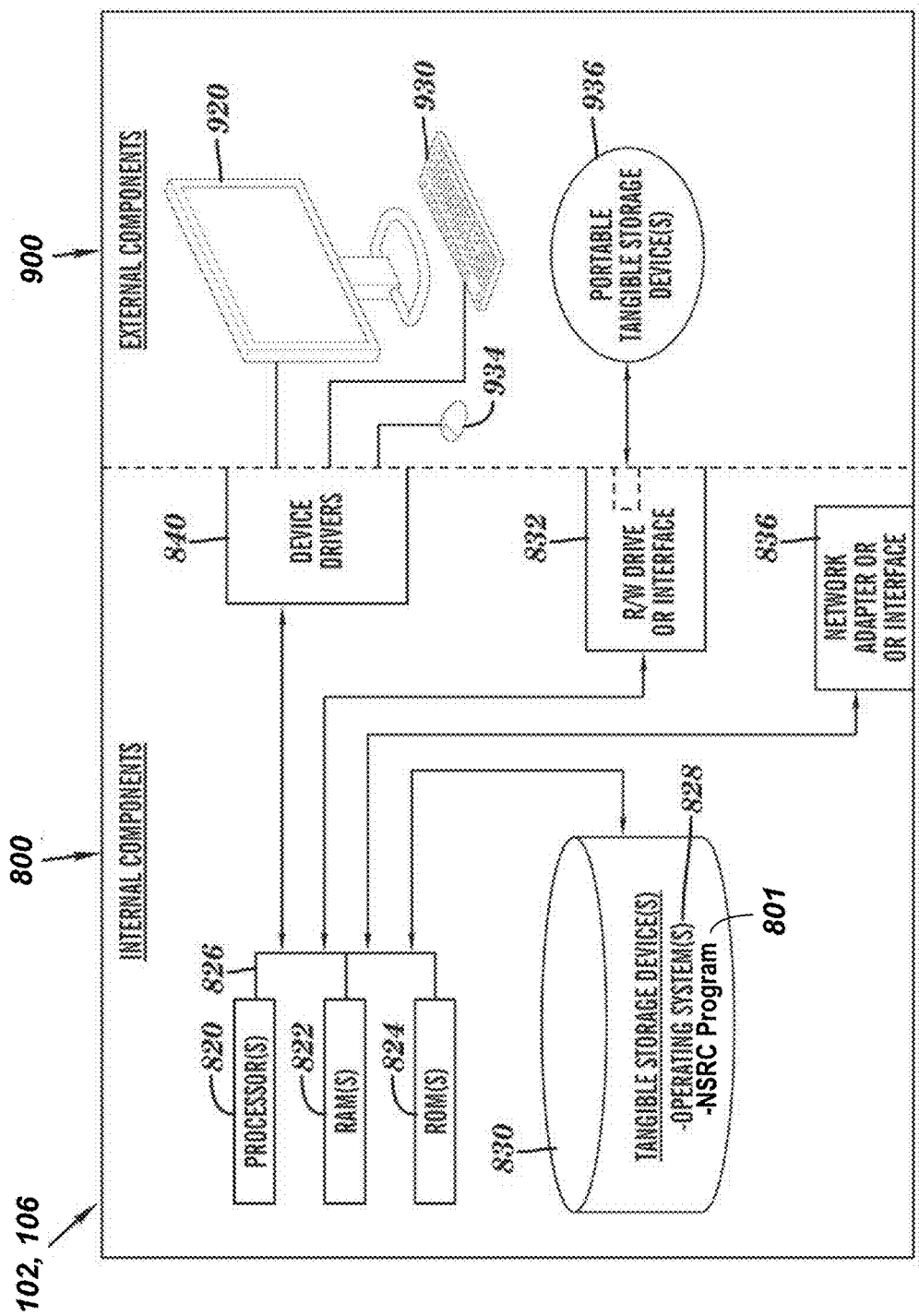
FIG. 8 is a block diagram of hardware and software for executing one or more the processes of FIGS. 3A-3D and/or FIG. 7, according to one embodiment.

FIG. 8 shows a block diagram of the components of a data processing system 800, 900, that may be incorporated within a processing component such as 106 (FIG. 1) and/or 108 (FIG. 1) in accordance with an illustrative embodiment of the present invention. It should be appreciated that FIG. 8 provides only an illustration of one implementation and does not imply any limitations with regard to the environments in which different embodiments may be implemented. Many modifications to the depicted environments may be made based on design and implementation requirements.

Data processing system 800, 900 is representative of any electronic device capable of executing machine-readable program instructions. Data processing system 800, 900 may be representative of a smart phone, a computer system, PDA, or other electronic devices. Examples of computing systems, environments, and/or configurations that may represented by data processing system 800, 900 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

The data processing system 800, 900 may include may include a set of internal components 800 and a set of external components 900 illustrated in FIG. 8. The set of internal components 800 includes one or more processors 820, one or more computer-readable RAMS 822 and one or more computer-readable ROMS 824 on one or more buses 826, and one or more operating systems 828 and one or more computer-readable tangible storage devices 830. The one or more operating systems 828 and programs such as neural signal recording control (NSRC) Program 801 (also see FIG. 7) and the processes of FIGS. 3A-3D can be stored on one or more computer-readable tangible storage devices 830 for execution by one or more processors 820 via one or more RAMS 822 (which typically include cache memory). In the embodiment illustrated in FIG. 8, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

The set of internal components 800 also includes a R/W drive or interface 832 to read from and write to one or more portable computer-readable tangible storage devices 936 such as a CD-ROM, DVD, memory stick, magnetic tape, magnetic disk, optical disk or semiconductor storage device. The NSRC program 801 can be stored on one or more of the respective portable computer-readable tangible storage devices 936, read via the respective R/W drive or interface 832 and loaded into the respective hard drive 830.

The set of internal components 800 may also include network adapters (or switch port cards) or interfaces 836 such as a TCP/IP adapter cards, wireless wi-fi interface cards, or 3G or 4G wireless interface cards or other wired or wireless communication links. NSRC program 801 and/or the processes of FIGS. 3A-3D can be downloaded from an external computer (e.g., server) via a network (for example, the Internet, a local area network or other, wide area network) and respective network adapters or interfaces 836. From the network adapters (or switch port adaptors) or interfaces 836, the NSRC program 801 and/or the processes of FIGS. 3A-3D are loaded into the respective hard drive 830. The network may comprise copper wires, optical fibers, wireless transmission, routers, firewalls, switches, gateway computers and/or edge servers.

The set of external components 900 can include a computer display monitor 920, a keyboard 930, and a computer mouse 934. External component 900 can also include touch screens, virtual keyboards, touch pads, pointing devices, and other human interface devices. The set of internal components 800 also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the one or more embodiment, the practical application or technical improvement over technologies found in the marketplace, or to enable others of ordinary skill in the art to understand the embodiments disclosed herein.

What is claimed is:

1. A neural signal recording device, comprising:
    a scan-mode circuit that detects neural spike activity at one or more M groups of electrodes selected from a total of N electrodes that are configured to be coupled to a brain; and
    a read-mode circuit that records all neural spike signals present at the one or more M groups of electrodes where the neural spike activity is detected by the scan-mode circuit,
    wherein less than N electrodes are recorded at any one time by the read-mode circuit;
    wherein the scan-mode circuit comprises:
    a plurality of M signal combining circuits that each combine neural spike signals from a group of C electrodes from the total of N electrodes configured to be coupled to the brain, and
    a plurality of M neural signal detection circuits that are each coupled to a respective one of the plurality of M signal combining circuits, the plurality of M neural signal detection circuits each detecting a presence of a neural spike signal on the group of C electrodes associated with the respective one of the plurality of M signal combining circuits; and
    wherein the read-mode circuit comprises:
    a switch matrix coupled to the N electrodes that routes the group of C electrodes associated with the respective one of the plurality of M signal combining circuits, the routing occurring in response to the detecting of the presence of the neural spike signal on the group of C electrodes associated with the respective one of the plurality of M signal combining circuits.

2. The device of claim 1, wherein the read-mode circuit further comprises:
    a digital signal processor device that receives and stores neural spike signals that are present on all of the routed group of C electrodes that are associated with the respective one of the plurality of M signal combining circuits that include the detected neural spike signal.

3. The device of claim 1, wherein the plurality of M signal combining circuits each comprise:
    a plurality of high-pass filter circuits that are each coupled to a respective one of the group of C electrodes and generate a filtered output;
    a power combiner circuit; and
    a switch control unit that controls a transmission of the filtered output from each of the plurality of high-pass filter circuits to the power combiner circuit,
    wherein the power combiner circuit aggregates filtered neural spike signals received from the group of C electrodes.

4. A method of recording neural spike signals from a brain, the method comprising:
    dividing N electrodes configured to be coupled to the brain into M groups, the M groups each having a plurality of electrodes;
    combining signals received from the plurality of electrodes corresponding to each one of the M groups of electrodes to generate M signal outputs;
    scanning all of the M signal outputs for a detection of neural spike signals; and
    responsive to the detection of the neural spike signals within any one or more of the M signal outputs, recording neural spike activity on all of the plurality of electrodes corresponding to the any one or more of the M groups of electrodes where the neural spike signals are detected,
    wherein less than N electrodes are recorded at any one time; and
    wherein the recording comprises:
    applying the N electrodes to a switch matrix having switch inputs and switch outputs;
    routing, from the switch inputs to the switch outputs, all the electrodes within any one or more of the M groups of electrodes corresponding to the any one or more of the M signal outputs on which the neural spike signals were detected; and digitizing any neural spike signals located at the switch outputs based on the routing of all the electrodes within any one or more of the M groups of electrodes corresponding to the any one or more of the M signal outputs on which the neural spike signals were detected.

5. The method of claim 4, wherein during the recording of the neural spike activity on all the electrodes within any one or more of the M groups of electrodes, the scanning for the detection of the neural spike signals within the any one or more of the M groups of electrodes is disabled.

6. The method of claim 4, wherein responsive to the detection of a presence of the neural spike signals, at least N/M electrodes and at most M electrodes are recorded at any one time.

7. The method of claim 4, wherein the detection of the neural spike signals comprise:
band-pass filtering signals received on each of the M signal outputs;
amplifying each of the band-pass filtered signals; and
converting each of the amplified signals to a digital format.

8. The method of claim 4, wherein the digitized neural spike signals are radio transmitted from a region of a skull encapsulating the brain.

9. The method of claim 4, further comprising:
dividing the M groups of one or more electrodes into $M_S$ groups of one or more electrodes and $M_R$ groups of one or more electrodes;
combining the one or more electrodes from each one of the $M_S$ groups of electrodes to generate $M_S$ signal outputs;
scanning all of the $M_S$ signal outputs for the detection of neural spike signals; and
responsive to the detection of the presence of the neural spike signals within any one or more of the $M_S$ signal outputs, recording neural spike activity on all electrodes within any one or more of the $M_S$ groups of electrodes corresponding to the any one or more of the $M_S$ signal outputs; and
recording neural spike activity on all electrodes within any one or more of the $M_R$ groups of electrodes.

10. The method of claim 9, wherein the scanning of all of the $M_S$ signal outputs occur simultaneously with the recording of the neural spike activity on all the electrodes within any one or more of the $M_R$ groups of electrodes.

11. A computer-implemented method of recording neural spike signals from a brain, the method comprising:
generating a scan control signal for enabling a receiving of a plurality of M output signals, wherein each of the plurality of M output signals are based on a combining of a plurality of input signals respectively received from a plurality of N electrodes configured to be coupled to the brain;
receiving digitized versions of the received plurality of M output signals for detecting neural spike signals from one or more of the plurality of M output signals; and
generating a read control signal for enabling a signal recording from all of the plurality of electrodes corresponding to the one or more of the plurality M output signals having the detected neural spike signals, wherein during the signal recording, the receiving of the plurality of output signals is disabled by the scan control signal, and wherein M<N;
further comprising:
generating a scan control signal for enabling receiving J of the M output signals, wherein each of the J of the M output signals are based on a combining of a plurality of input signals received from a first group of the plurality of N electrodes;
receiving digitized versions of a plurality of J output signals for detecting neural spike signals from one or more of the plurality of J output signals;
generating a first read control signal for enabling a signal recording from the plurality of input signals received from the first group of the plurality of N electrodes that respectively correspond to the one or more of the plurality of J output signals having the detected neural spike signals; and
generating a second read control signal for enabling a signal recording from a plurality of input signals received from a second group of the plurality of N electrodes, wherein the second group of the plurality of N electrodes are respectively recorded via the M output signals and the J output signals.

12. The computer-implemented method of claim 11, wherein the signal recording is enabled by controlling a routing of all of the plurality of electrodes corresponding to the one or more of the plurality of M output signals having the detected neural spike signals to a digital signal processor via a switch matrix.

13. A computer program product for recording neural spike signals from a brain, the computer program product comprising:
one or more non-transitory computer-readable storage devices and program instructions stored on at least one of the one or more non-transitory storage devices, the program instructions executable by a processor, the program instructions comprising:
instructions to generate a scan control signal for enabling a receiving of a plurality of M output signals, wherein each of the plurality of M output signals are based on a combining of a plurality of input signals respectively received from a plurality of N electrodes configured to be coupled to the brain;
instructions to receive digitized versions of the received plurality of M output signals for detecting neural spike signals from one or more of the plurality of M output signals; and
instructions to generate a read control signal for enabling a signal recording from all of the plurality of electrodes corresponding to the one or more of the plurality of M output signals having the detected neural spike signals, wherein during the signal recording, the receiving of the plurality of output signals is disabled by the scan control signal, and wherein M<N;
further comprising:
instructions to generate a scan control signal for enabling receiving J of the M output signals, wherein each of the J of the M output signals are based on a combining of a plurality of input signals received from a first group of the plurality of N electrodes;
instructions to receive digitized versions of a plurality of J output signals for detecting neural spike signals from one or more of the plurality of J output signals;
instructions to generate a first read control signal for enabling a signal recording from the plurality of input signals received from the first group of the plurality of N electrodes that respectively corresponds to the one or more of the plurality of J output signals having the detected neural spike signals; and
instructions to generate a second read control signal for enabling a signal recording from a plurality of input signals received from a second group of the plurality of N electrodes, wherein the second group of the plurality of N electrodes are respectively recorded via the M output signals and the J output signals.

\* \* \* \* \*